US010065977B2

(12) United States Patent
Humbarger et al.

(10) Patent No.: US 10,065,977 B2
(45) Date of Patent: Sep. 4, 2018

(54) CONCERTED PROCESSES FOR FORMING 1,2,4-TRIHYDROXYBENZENE FROM HYDROQUINONE

(71) Applicant: LOCKHEED MARTIN ADVANCED ENERGY STORAGE, LLC, Bethesda, MD (US)

(72) Inventors: Scott Thomas Humbarger, Cambridge, MA (US); Matthew Millard, Cambridge, MA (US)

(73) Assignee: Lockheed Martin Advanced Energy Storage, LLC, Bethesda, MD (US)

( * ) Notice: Subject to any disclaimer, the term of this patent is extended or adjusted under 35 U.S.C. 154(b) by 3 days.

(21) Appl. No.: 15/298,175

(22) Filed: Oct. 19, 2016

(65) Prior Publication Data

US 2018/0105544 A1    Apr. 19, 2018

(51) Int. Cl.
| | | |
|---|---|---|
| C07C 46/06 | (2006.01) | |
| C07F 7/28 | (2006.01) | |
| C07C 46/10 | (2006.01) | |
| C07C 67/00 | (2006.01) | |
| C07C 67/56 | (2006.01) | |
| C07C 37/56 | (2006.01) | |
| C07C 37/82 | (2006.01) | |

(52) U.S. Cl.
CPC ............ *C07F 7/28* (2013.01); *C07C 37/56* (2013.01); *C07C 37/82* (2013.01); *C07C 46/06* (2013.01); *C07C 46/10* (2013.01); *C07C 67/00* (2013.01); *C07C 67/56* (2013.01)

(58) Field of Classification Search
USPC .............................................. 556/51, 54, 55
See application file for complete search history.

(56) References Cited

U.S. PATENT DOCUMENTS

| | | |
|---|---|---|
| 1,279,295 A | 9/1918 | Downs |
| 2,353,782 A | 7/1944 | Neumark |
| 2,415,792 A | 2/1947 | Gravell |
| 3,294,588 A | 12/1966 | Morton |
| 3,425,796 A | 2/1969 | Bauer |
| 3,428,654 A | 2/1969 | Rubinfeld |
| 3,573,984 A | 4/1971 | Shah |
| 3,707,449 A | 12/1972 | Reinhardt et al. |
| 3,772,379 A | 11/1973 | Woodgate |
| 3,876,435 A | 4/1975 | Dollman |
| 3,916,004 A | 10/1975 | Okada et al. |
| 3,919,000 A | 11/1975 | Yarrington |
| 3,920,756 A * | 11/1975 | Tahara ................... C07C 37/60 502/167 |
| 3,929,506 A | 12/1975 | Leddy et al. |
| 3,985,517 A | 10/1976 | Johnson |
| 3,985,585 A | 10/1976 | Tuttle et al. |
| 4,046,861 A | 9/1977 | Reinhardt et al. |
| 4,064,324 A | 12/1977 | Eustace |
| 4,069,371 A | 1/1978 | Zito |
| 4,126,529 A | 11/1978 | DeBerry |
| 4,180,623 A | 12/1979 | Adams |
| 4,202,799 A | 5/1980 | Yoshimura et al. |
| 4,233,144 A | 11/1980 | Pace et al. |
| 4,362,791 A | 12/1982 | Kaneko et al. |
| 4,378,995 A | 4/1983 | Gratzfeld et al. |
| 4,410,606 A | 10/1983 | Loutfy et al. |
| 4,436,711 A | 3/1984 | Olson |
| 4,436,712 A | 3/1984 | Olson |
| 4,436,713 A | 3/1984 | Olson |
| 4,436,714 A | 3/1984 | Olson |
| 4,443,423 A | 4/1984 | Olson |
| 4,443,424 A | 4/1984 | Olson |
| 4,468,441 A | 8/1984 | D'Agostino et al. |
| 4,485,154 A | 11/1984 | Remick et al. |
| 4,520,083 A | 5/1985 | Prater et al. |
| 4,563,403 A | 1/1986 | Julian |
| 4,592,973 A | 6/1986 | Pemsler et al. |
| 4,617,244 A | 10/1986 | Greene |
| 4,680,308 A | 7/1987 | Schwartz et al. |
| 4,818,646 A | 4/1989 | Takakubo et al. |
| 4,880,758 A | 11/1989 | Heistand, II et al. |
| 4,952,289 A | 8/1990 | Ciccone et al. |
| 4,959,135 A | 9/1990 | Zenner et al. |
| 4,973,720 A * | 11/1990 | Saito ....................... C07C 46/06 552/293 |
| 5,084,533 A | 1/1992 | Shah et al. |
| 5,122,461 A | 6/1992 | Hsiung et al. |
| 5,264,097 A | 11/1993 | Vaughan |
| 5,302,481 A | 4/1994 | Ong |
| 5,318,865 A | 6/1994 | Kaneko et al. |
| 5,433,934 A | 7/1995 | Chang et al. |
| 5,472,807 A | 12/1995 | Licht et al. |

(Continued)

FOREIGN PATENT DOCUMENTS

| | | |
|---|---|---|
| CN | 1284208 A | 2/2001 |
| CN | 101877412 A | 11/2010 |

(Continued)

OTHER PUBLICATIONS

Ahluwalia; Intermediates for Organic Synthesis; Chapter 1, Phenols, Section 1.21 and 1.23.*

(Continued)

*Primary Examiner* — Pancham Bakshi
(74) *Attorney, Agent, or Firm* — Baker & Hostetler LLP

(57) ABSTRACT

Flow batteries incorporating an active material with one or more catecholate ligands can have a number of desirable operating features. Commercial syntheses of catechol produce significant quantities of hydroquinone as a byproduct, which presently has limited value in the battery industry and can represent a significant waste disposal issue at industrial production scales. Using a concerted, high-yield process, low-value hydroquinone can be transformed into high-value 1,2,4-trihydroxybenzene, which can be a desirable ligand for active materials of relevance in the flow battery industry. Methods for forming 1,2,4-trihydroxybenzene can include: oxidizing hydroquinone in a first reaction to form p-benzoquinone, converting the p-benzoquinone in a second reaction to form 1,2,4-triacetoxybenzene, deacetylating the 1,2,4-triacetoxybenzene in a third reaction to form 1,2,4-trihydroxybenzene, and isolating the 1,2,4-trihydroxybenzene after performing the first reaction, the second reaction and the third reaction consecutively.

19 Claims, 6 Drawing Sheets

(56) References Cited

U.S. PATENT DOCUMENTS

| | | |
|---|---|---|
| 5,643,670 A | 7/1997 | Chung |
| 5,679,239 A | 10/1997 | Blum et al. |
| 5,759,711 A | 6/1998 | Miyabayashi et al. |
| 5,785,841 A | 7/1998 | Tseng |
| 5,876,581 A | 3/1999 | Itaya et al. |
| 5,910,366 A | 6/1999 | Chowdhury et al. |
| 6,001,326 A | 12/1999 | Kim et al. |
| 6,030,517 A | 2/2000 | Lincot et al. |
| 6,054,230 A | 4/2000 | Kato |
| 6,461,772 B1 | 10/2002 | Miyake et al. |
| 6,475,661 B1 | 11/2002 | Pellegri et al. |
| 6,485,868 B1 | 11/2002 | Tsujioka et al. |
| 6,555,989 B1 | 4/2003 | Pearson |
| 6,585,951 B1 | 7/2003 | Hong et al. |
| 6,624,328 B1 | 9/2003 | Guerra |
| 7,046,418 B2 | 5/2006 | Lin et al. |
| 7,193,764 B2 | 3/2007 | Lin et al. |
| 7,223,833 B1 | 5/2007 | Nielsen et al. |
| 7,252,905 B2 | 8/2007 | Clarke et al. |
| 7,265,162 B2 | 9/2007 | Yandrasits et al. |
| 7,348,088 B2 | 3/2008 | Hamrock et al. |
| 7,463,917 B2 | 12/2008 | Martinez |
| 7,508,568 B2 | 3/2009 | Lin et al. |
| 7,550,231 B2 | 6/2009 | Stauffer |
| 7,557,164 B2 | 7/2009 | Felix et al. |
| 7,625,663 B2 | 12/2009 | Clarke et al. |
| 7,645,540 B2 | 1/2010 | Boone et al. |
| 7,678,728 B2 | 3/2010 | Olson et al. |
| 7,745,056 B2 | 6/2010 | Lee et al. |
| 7,767,777 B2 | 8/2010 | Buesing et al. |
| 7,927,731 B2 | 4/2011 | Sahu |
| 7,931,981 B2 | 4/2011 | Boone et al. |
| 7,935,366 B2 | 5/2011 | Pahuja et al. |
| 7,998,335 B2 | 8/2011 | Feeney et al. |
| 8,129,554 B2 | 3/2012 | Schwaiger |
| 8,187,441 B2 | 5/2012 | Evans et al. |
| 8,445,118 B2 | 5/2013 | Cordonier et al. |
| 8,492,581 B2 | 7/2013 | Frost |
| 8,691,413 B2 | 4/2014 | Esswein et al. |
| 8,753,761 B2 | 6/2014 | Esswein et al. |
| 9,300,000 B2 | 3/2016 | Jansen et al. |
| 9,382,274 B2 | 7/2016 | Esswein et al. |
| 9,409,842 B1 | 8/2016 | Fu et al. |
| 2002/0177042 A1 | 11/2002 | Amendola |
| 2003/0068561 A1 | 4/2003 | Okahara et al. |
| 2003/0143456 A1 | 7/2003 | Kazacos et al. |
| 2003/0228394 A1 | 12/2003 | Abdel-Monem et al. |
| 2004/0096746 A1 | 5/2004 | Wietelmann et al. |
| 2005/0098437 A1 | 5/2005 | Shiepe |
| 2005/0244707 A1 | 11/2005 | Skyllas-Kazacos et al. |
| 2006/0047094 A1 | 3/2006 | Cherkasov et al. |
| 2007/0275291 A1 | 11/2007 | Gu et al. |
| 2008/0274385 A1 | 11/2008 | Creeth |
| 2008/0292964 A1 | 11/2008 | Kazacos et al. |
| 2009/0110998 A1 | 4/2009 | Miyachi et al. |
| 2009/0130525 A1 | 5/2009 | Miyachi et al. |
| 2009/0208807 A1 | 8/2009 | Miyachi et al. |
| 2009/0308752 A1 | 12/2009 | Evans et al. |
| 2010/0003586 A1 | 1/2010 | Sahu |
| 2010/0059388 A1 | 3/2010 | Clarke et al. |
| 2010/0086823 A1 | 4/2010 | Koshino et al. |
| 2010/0086983 A1 | 4/2010 | Gellett et al. |
| 2010/0239946 A1 | 9/2010 | Miyachi et al. |
| 2011/0014532 A1 | 1/2011 | Knuckey et al. |
| 2011/0136016 A1 | 6/2011 | Huang et al. |
| 2011/0189549 A1 | 8/2011 | Sun et al. |
| 2011/0195283 A1 | 8/2011 | Sun et al. |
| 2011/0200890 A1 | 8/2011 | Kocherginsky |
| 2011/0223450 A1 | 9/2011 | Horne et al. |
| 2011/0244277 A1 | 10/2011 | Gordon, II et al. |
| 2011/0244367 A1 | 10/2011 | Watahiki et al. |
| 2012/0052347 A1 | 3/2012 | Wilson et al. |
| 2012/0077095 A1 | 3/2012 | Roumi et al. |
| 2012/0107661 A1 | 5/2012 | Lee et al. |
| 2012/0135278 A1 | 5/2012 | Yoshie et al. |
| 2012/0171541 A1 | 7/2012 | Park et al. |
| 2012/0183868 A1 | 7/2012 | Toussaint et al. |
| 2012/0196188 A1 | 8/2012 | Zhang et al. |
| 2012/0202099 A1 | 8/2012 | Perry et al. |
| 2012/0208061 A1 | 8/2012 | Sahu et al. |
| 2012/0244406 A1 | 9/2012 | Xia et al. |
| 2012/0263990 A1 | 10/2012 | Kim |
| 2013/0004819 A1 | 1/2013 | Mun et al. |
| 2013/0157087 A1 | 6/2013 | Pandy et al. |
| 2013/0252062 A1 | 9/2013 | Wilkins et al. |
| 2013/0252137 A1 | 9/2013 | Zhang et al. |
| 2014/0028260 A1 | 1/2014 | Goeltz et al. |
| 2014/0028261 A1 | 1/2014 | Esswein et al. |
| 2014/0030572 A1 | 1/2014 | Esswein et al. |
| 2014/0030573 A1 | 1/2014 | Esswein et al. |
| 2014/0030631 A1 | 1/2014 | Esswein et al. |
| 2014/0051003 A1 | 2/2014 | Esswein et al. |
| 2014/0080035 A1 | 3/2014 | Esswein et al. |
| 2014/0138576 A1* | 5/2014 | Esswein .................. C07F 7/28 252/182.1 |
| 2014/0178735 A1 | 6/2014 | Wang et al. |
| 2014/0193687 A1 | 7/2014 | Park et al. |
| 2014/0239906 A1 | 8/2014 | Anderson et al. |
| 2014/0274936 A1 | 9/2014 | Piccariello et al. |
| 2014/0349177 A1 | 11/2014 | Chung et al. |
| 2014/0377666 A1 | 12/2014 | Kodama et al. |
| 2015/0236543 A1 | 8/2015 | Brushett et al. |
| 2015/0372333 A1 | 12/2015 | Odom et al. |
| 2016/0066578 A1 | 3/2016 | Ala'Aldeen et al. |
| 2016/0149251 A1 | 5/2016 | Reece |
| 2016/0208165 A1 | 7/2016 | Li et al. |
| 2016/0264603 A1 | 9/2016 | Esswein et al. |
| 2016/0268623 A1 | 9/2016 | Esswein et al. |
| 2016/0272659 A1 | 9/2016 | King et al. |
| 2016/0276693 A1 | 9/2016 | Goeltz et al. |
| 2016/0276694 A1 | 9/2016 | Goeltz et al. |
| 2016/0276695 A1 | 9/2016 | Esswein et al. |
| 2017/0253620 A1 | 9/2017 | Humbarger et al. |
| 2017/0256811 A1 | 9/2017 | Humbarger et al. |
| 2017/0271704 A1 | 9/2017 | Morris-Cohen |

FOREIGN PATENT DOCUMENTS

| | | |
|---|---|---|
| EP | 0814527 A2 | 12/1997 |
| EP | 1290068 A2 | 3/2003 |
| EP | 1411576 A1 | 4/2004 |
| EP | 1901379 A1 | 3/2008 |
| EP | 2235781 A1 | 10/2010 |
| EP | 2463950 A1 | 6/2012 |
| FR | 1533662 A | 7/1968 |
| GB | 1354886 A | 6/1974 |
| WO | WO-95/12219 A1 | 5/1995 |
| WO | WO-1997/017354 A1 | 5/1997 |
| WO | WO-2004/095602 A2 | 11/2004 |
| WO | WO-2006/135958 A1 | 12/2006 |
| WO | WO-2007/044852 A2 | 4/2007 |
| WO | WO-2007/101284 A1 | 9/2007 |
| WO | WO-2011/075135 A1 | 6/2011 |
| WO | WO-2011/098781 A1 | 8/2011 |
| WO | WO-2011/149624 A1 | 12/2011 |
| WO | WO-2012/075810 A1 | 6/2012 |
| WO | WO-2013/006427 A1 | 1/2013 |
| WO | WO-2013/048603 A1 | 4/2013 |
| WO | WO-2015/069439 A1 | 5/2015 |

OTHER PUBLICATIONS

Borgias, "Synthetic, structural, and physical studies of titanium complexes of catechol and 3,5-di-tert-butylcatechol," Inorg. Chem., Apr. 1984, 23(8), 1009-1016.

Brezina, "Study of the reduction of oxygen on a carbon paste electrode in an alkaline medium," Coll. Czech. Chem. Commun., 1973, 38(10), 3024-3031.

Caulton, "Systematics and Future Projections Concerning Redox-Noninnocent Amide/Imine Ligands," Eur. J. Inorg. Chem., Jan. 2012, 2012(3), 435-443.

(56) References Cited

OTHER PUBLICATIONS

Cerofontain et al. "Sulfonation and sulfation on reaction of 1,2-dihydroxybenzene and its methyl ethers in concentrated aqueous sulfuric acid," Recl Tray Chim Pays-Bas, 1988, pp. 325-330, vol. 107.
Chen, "Solution Redox Couples for Electrochemical Energy Storage: I. Iron (III)-Iron (II) Complexes with O-Phenanthroline and Related Ligands," Journal of the Electrochemical Society, Jul. 1981, 128(7), 1460-1467.
Cohen, "The Association of Ferrocyanide Ions With Various Cations," J. Phys. Chem., Aug. 1957, 61(8), 1096-1100.
Davies, "Eiectroceramics from Source Materials via Molecular Intermediates: PbTi03 from Ti02 via [Ti(catecholate)3]2-" J. Am. Ceram. Soc., Aug. 1990, 73(8), 2570-2572.
Dehaen et al, "A Self-Assembled Complex with a Titanium (IV) Catecholate Core as a Potential Bimodal Contrast Agent," Chem Eur J, 2012, pp. 293-302, vol. 18.
Fryda, "Wastewater Treatment With Diamond Electrodes," Diamond Materials, Electrochemical Society Proceedings, 2000, 99(32), 473-483.
Gail, "Cyano Compounds, Inorganic" in Ullmann's Encyclopedia of Industrial Chemistry, 2012, 10, 674-710.
Hollandsworth, "Zinc/Ferrocyanide Battery Development Phase IV" Lockheed Missiles and Space Company, Inc., Contractor report, Sandia Contract DE-AC04-76DP00789, May 1985, 278 pages.
Kim, "Novel catalytic effects of Mn304 for all vanadium redox flow batteries," Chem. Commun., Apr. 2012, 48(44), 5455-5457.
Kulesza, "Electrochemical preparation and characterization of hybrid films composed of Prussian blue type metal hexacyanoferrate and conducting polymer," Electrochimica Acta, Aug. 2001, 46(26-27), 4065-4073.
Leung, "Development of a Zinc—Cerium Redox Flow Battery", 2011, 352 pages.
Leung, "An undivided zinc—cerium redox flow battery operating at room temperature (295 K)," Electrochemistry Communications, 2011, vol. 13, pp. 770-773.
Leung, "Ce(III)/Ce(iV) in methanesulfonic acid as the positive half cell of a redox flow battery," Electrochimica Acta, 2011, vol. 56, pp. 2145-2153.
Leung, "Zinc deposition and dissolution in methanesulfonic acid onto a carbon composite electrode as the negative electrode reactions in a hybrid redox flow battery," Electrochimica Acta, 2011, vol. 56, pp. 6536-6546.
Leung, "Characterization of a zinc—cerium flow battery," Journal of Power Sources, 2011, vol. 195, pp. 5174-5185.
Modiba, "Electrochemical impedance spectroscopy study of Ce(IV) with aminopolycarboxylate ligands for redox flow batteries applications," Journal of Power Sources, May 2012, vol. 205, 1-9.
Modiba, "Electrochemical study of cerium(IV) in the presence of ethylenediaminetetraacetic acid (EDTA) and diethylenetriaminepentaacetate (DTPA) ligands," Journal of Applied Electrochemistry, Sep. 2008, 38(9), 1293-1299.
Modiba, "Electrolytes for redox flow battery systems," Dissertation presented for the degree of Doctor of Philosophy Chemistry at the University of Stellenbosch, Department of Chemistry and Polymer Science, Mar. 2010.
Nguyen, "Flow Batteries," The Electrochemical Society Interface, Fall2010, 19(3), 54-56.
Pharr, "Infrared Spectroelectrochemical Analysis of Adsorbed Hexacyanoferrate Species Formed during Potential Cycling in the Ferrocyanide/Ferricyanide Redox Couple," Anal. Chem., Nov. 1997, 69(22), 4673-4679.
Raymond , "Coordination isomers of biological iron transport compounds. VI. Models of the enterobactin coordination site. A crystal field effect in the structure of potassium tris( catecholato ) chromate( III) and -ferrate( III) sesq u ihyd rates, K3 [M( 02C6H4 )3]. 1 . 5H20, M=chromium, iron," J. Am. Chem. Soc., Mar. 1976, 98(7), 1767-1774.

Saito et al. "DPPH radical-scavenging reaction of protocatechuic acid: differnce in reactivity between acids and their esters," Helv Chim Acta, 2006, is 1395-1407, vol. 89.
Sever et al, "Visible absorption spectra of metal-catecholate and metal-tironate complexes," Dalton Trans., pp. 1061-1072, 2004.
Sigma-Aldrich Tris(hydroxymethl)aminomethane, 2015.
Sommer, "Titanium (IV) complexes with ligands having oxygen donor atoms in aqueous solutions," Zeitschrift fur Anorganische and Aligemeine Chemie, Mar. 1963, pp. 191-197, vol. 321, issue 3-4.
Steenken, "One-electron redox potentials of phenols. Hydroxy- and aminophenols and related compounds of biological interest," J. Phys. Chem., Sep. 1982, 86(18), 3661-3667.
Torres-Gomez, "Energy Storage in Hybrid Organic-Inorganic Materials Hexacyanoferrate-Doped Polypyrrole as Cathode in Reversible Lithium Cells," J. of the Electrochemical Society, 2000, 147(7), 2513-2516.
Trant, "Solubility of Sodium Ferrocyanide and Potassium Ferrocyanide in Solutions of NaOH and KOH Mixtures at 25.degree. C," University of Rochester, The David T. Kearns Center, Xerox Undergraduate Research Fellows Program, Jul. 28, 2011, 1 page.
Vercillo, "Solubility of Sodium Ferrocyanide in Sodium Hydroxide and Potassium Ferrocyanide in Potassium Hydroxide," University of Rochester, The David T. Kearns Center, Xerox Undergraduate Research Fellows Program, Jul. 28, 2011, 1 page.
Wang, "Determination of iron, titanium, osmium, and aluminum with tiron by reversephase high Performance liquid chromatography/electrochemistry," Microchem. J., Jun. 1991, 43(3), 191-197.
Weber, "Redox flow batteries: a review," Journal of Applied Electrochemistry, Oct. 2011, 41(10), 1137-1164.
Murakami et al., "The Chelating Behavior of Catechol-4-sulfonate with Iron(III) Ion," Bulletin of the Chemical Society of Japan, 1963, pp. 1408-1411; vol. 36.
Westervelt, "A Study of the Calcium Complex of the Potassium Salt of Catechol-4-Sulfonate in Aqueous, Alkalino Media," Jan. 1981, Doctoral Dissertation, retrieved from https://smartech.gatech.edu/bitstream/handle/1853/5723/westervelt-iii_hh.pdf.
E. Bosch, et al., "Novel Catalysis of Hydroquinone Autoxidation with Nitrogen Oxides," J. Org. Chem., 1994, pp. 2529-2536, 59.
M. Lang, et al., "Studies on the Structure and Biosynthesis of Tridentoquinone and Related Meroterpenoids from the Mushroom *Suillus tridentinus* (Boletales)," Eur. J. Org. Chem., 2008, pp. 816-825., 2008.
Y.-H. Ahn, et al., "A Study of Benzene 1,2,4-Trisphosphate Derivatives as Inositol 1,4,5-Trisphosphate 3-Kinase Inhibitors," Bull. Korean Chem. Soc., 2002, pp. 515-517, vol. 23., No. 3.
M. Lang, et al., "Studies on the Biosynthesis of Bovilactone-4,4 and Related Fungal Meroterpenoids," Eur. J. Org. Chem., 2008, pp. 3544-3551, 2008.
S. Spyroudis, "Hydroxyquinones: Synthesis and Reactivity," Molecules, 2000, pp. 1291-1330, 5.
J.F.W. McOmie, et al. "The Thiele-Winter Acetoxylation of Quinones," Organic Reactions, 1972, pp. 199-277, 19, John Wiley and Sons, Inc., New York.
Ali et al., "Synthesis and Processing Characteristics of $Ba_{0.65}Sr_{0.35}TiO_3$ Powders from Catecholate Precursors," J Am Ceram Soc, 1993, pp. 2321-2326, vol. 76, No. 9.
Devi et al., "pH-metric investigation on Mixed-Ligand Complexes of Ca(II), Mg(II) and Zn(II) with L-Dopa and 1,10 Phenantroline in Propylene glycol-Water Mixtures," RRJC, Oct.-Dec. 2012, vol. 1, Issue 1, pp. 13-22.
Xu, "Mechanics of metal-catecholate complexes: The roles of coordination state and metal types," Scientific Reports, Oct. 10, 2013, 3:2914, pp. 1-7.
Soloveichik, "Flow Batteries: Current Status and Trends," 2015, Chem. Rev., 115 (20), pp. 11533-11558.
Davies, "Eiectroceramics from Source Materials via Molecular Intermediates: $BaTl0_3$ from $Tl0_2$ via $[Ti(catecholate)_3]^{2-}$," May 1990, J. Am. Ceram. Soc., Aug. 1990, 73(5), 1429-30.
Abdulghani et al., "Preparation and Characterization of Di-, Tri-, and Tetranuclear Schiff Base Complexes Derived from Diamines and 3,4-Dihydroxybenzaldehyde," Hindawi Publishing Corp, Bioinorganic Chemistry and Applications, 2013, pp. 1-14.

(56) References Cited

OTHER PUBLICATIONS

IUPAC Compendium of Chemical Terminology, "coordinatively unsaturated complex," 1997, http://old.iupac.org/goldbook/C01334.pdf.
Mansoor, "Mixed Metal Complexes of Copper (II), Nickel (II) and Zinc (II) Involving Dopa and Dopamine," International Journal of ChemTech Research, Jan.-Mar. 2010, vol. 2, No. 1, pp. 640-645.
International Search Resort and Written Opinion from PCT/US17/14764, dated Apr. 20, 2017.
International Search Report and Written Opinion from PCT/US16/69190, dated May 3, 2017.
International Search Report and Written Opinion from PCT/US2017/022203, dated Jun. 6, 2017.
Ahluwalia et al., Intermediates for Organic Synthesis, Chapter 1, Phenols, Sections 1.21 and 1.23, (2003), I.K. International Pvt. Ltd.
Vliet et al., "Hydroxyhydroquinone Triacetate," Organic Synthesys, 1941, Coll vol. 1, p. 317 (1941), vol. 4, p. 35 (1925) 3 pages.
International Search Report and Written Opinion dated Jan. 19, 2017 from International Application No. PCT/US16/58433.
International Search Report and Written Opinion dated Feb. 17, 2017 from International Application No. PCT/US16/65159.
Wang et al., "Issues in Freeze Drying of Aqueous Solutions," Chinese Journal of Chemical Engineering, 2012, 20(3), pp. 551-559.

\* cited by examiner

CONCERTED PROCESSES FOR FORMING 1,2,4-TRIHYDROXYBENZENE FROM HYDROQUINONE

CROSS-REFERENCE TO RELATED APPLICATIONS

Not applicable.

STATEMENT REGARDING FEDERALLY SPONSORED RESEARCH OR DEVELOPMENT

Not applicable.

FIELD

The present disclosure generally relates to energy storage and, more specifically, to methods for processing hydroquinone into 1,2,4-trihydroxybenzene and coordination complexes related thereto.

BACKGROUND

Electrochemical energy storage systems, such as batteries, supercapacitors and the like, have been widely proposed for large-scale energy storage applications. Various battery designs, including flow batteries, have been considered for this purpose. Compared to other types of electrochemical energy storage systems, flow batteries can be advantageous, particularly for large-scale applications, due to their ability to decouple the parameters of power density and energy density from one another.

Flow batteries generally include negative and positive active materials in corresponding electrolyte solutions, which are flowed separately across opposing sides of a membrane or separator in an electrochemical cell containing negative and positive electrodes. The flow battery is charged or discharged through electrochemical reactions of the active materials that occur inside the two half-cells. As used herein, the terms "active material," "electroactive material," "redox-active material" or variants thereof synonymously refer to materials that undergo a change in oxidation state during operation of a flow battery or like electrochemical energy storage system (i.e., during charging or discharging). Although flow batteries hold significant promise for large-scale energy storage applications, they have often been plagued by sub-optimal energy storage performance (e.g., round trip energy efficiency) and limited cycle life, among other factors. Despite significant investigational efforts, no commercially viable flow battery technologies have yet been developed.

Metal-based active materials can often be desirable for use in flow batteries and other electrochemical energy storage systems. Although non-ligated metal ions (e.g., dissolved salts of a redox-active metal) can be used as an active material, it can often be more desirable to utilize coordination complexes for this purpose. As used herein, the terms "coordination complex, "coordination compound," "metal-ligand complex," or simply "complex" synonymously refer to a compound having at least one covalent bond formed between a metal center and a donor ligand. The metal center can cycle between an oxidized form and a reduced form in an electrolyte solution, where the oxidized and reduced forms of the metal center represent states of full charge or full discharge depending upon the particular half-cell in which the coordination complex is present.

Metal catecholate complexes can be particularly desirable active materials, since they are relatively stable complexes, have relatively good solubility in aqueous media, and can provide flow batteries having efficient operating characteristics. In some instances, metal catecholate complexes containing only unsubstituted catecholate ligands can be suitable for use within flow batteries. In other cases, substituted catechol compounds having solubilizing groups thereon can improve the aqueous solubility of coordination complexes where they are present. The syntheses of such substituted catechol compounds can frequently proceed from catechol itself (i.e., 1,2-dihydroxybenzene). Although catechol is a relatively inexpensive commodity chemical, a significant amount of hydroquinone byproduct is frequently co-produced in commercial catechol syntheses. While hydroquinone can be separated from catechol prior to incorporation of the latter in coordination complexes, the hydroquinone byproduct represents a significant feedstock waste in terms of atom economy. Moreover, the hydroquinone byproduct presents a substantial waste disposal issue when taking into account the multi-ton quantities of active materials that are anticipated to be needed in support of commercial flow battery applications. At present, the hydroquinone byproduct has no significant use in the flow battery industry.

In view of the foregoing, processes for converting a hydroquinone byproduct into a higher-value material, particularly a material of relevance to the flow battery industry, would be highly desirable in the art. The present disclosure satisfies the foregoing needs and provides related advantages as well.

SUMMARY

In various embodiments, methods for synthesizing 1,2,4-trihydroxybenzene include: oxidizing hydroquinone in a first reaction to form p-benzoquinone, converting the p-benzoquinone in a second reaction to form 1,2,4-triacetoxybenzene, deacetylating the 1,2,4-triacetoxybenzene in a third reaction to form 1,2,4-trihydroxybenzene, and isolating the 1,2,4-trihydroxybenzene after performing the first reaction, the second reaction and the third reaction consecutively.

The foregoing has outlined rather broadly the features of the present disclosure in order that the detailed description that follows can be better understood. Additional features and advantages of the disclosure will be described hereinafter. These and other advantages and features will become more apparent from the following description.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Figure 1:
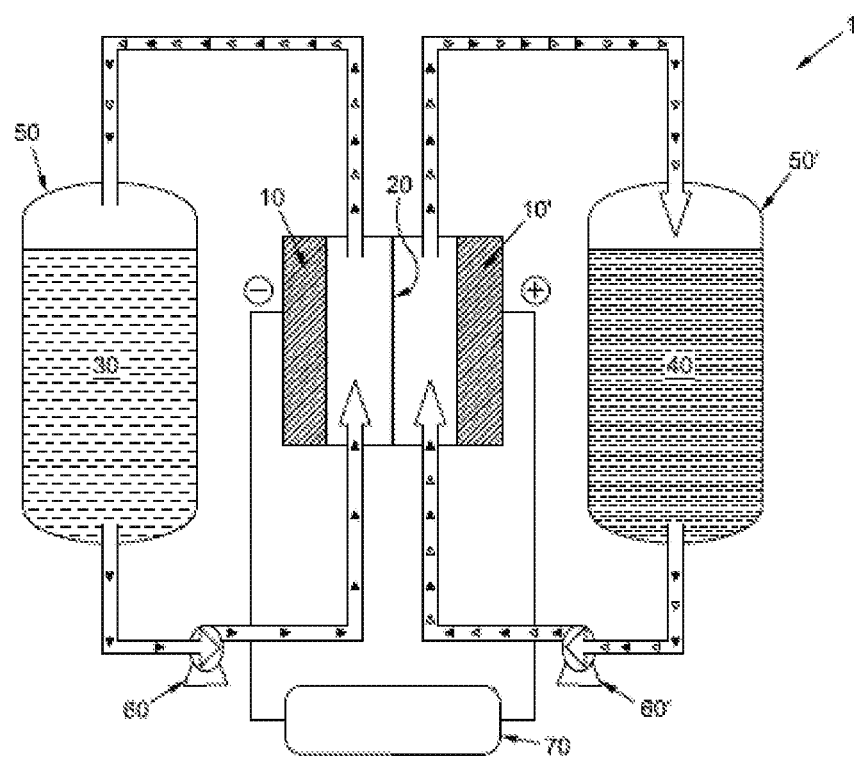
FIG. 1 depicts a schematic of an illustrative flow battery.

The present disclosure is directed, in part, to methods for synthesizing 1,2,4-trihydroxybenezene from hydroquinone. The present disclosure is also directed, in part, to methods for synthesizing coordination complexes containing 1,2,4-trihydroxybenzene as a ligand. The present disclosure is also directed, in part, to flow batteries containing at least one active material that is a coordination complex containing 1,2,4-trihydroxybenzene as a ligand.

The present disclosure may be understood more readily by reference to the following description taken in connection with the accompanying figures and examples, all of which form a part of this disclosure. It is to be understood that this disclosure is not limited to the specific products, methods, conditions or parameters described and/or shown herein. Further, the terminology used herein is for purposes of describing particular embodiments by way of example only and is not intended to be limiting unless otherwise specified. Similarly, unless specifically stated otherwise, any description herein directed to a composition is intended to refer to both solid and liquid versions of the composition, including solutions and electrolytes containing the composition, and electrochemical cells, flow batteries, and other energy storage systems containing such solutions and electrolytes. Further, it is to be recognized that where the disclosure herein describes an electrochemical cell, flow battery, or other energy storage system, it is to be appreciated that methods for operating the electrochemical cell, flow battery, or other energy storage system are also implicitly described.

It is also to be appreciated that certain features of the present disclosure may be described herein in the context of separate embodiments for clarity purposes, but may also be provided in combination with one another in a single embodiment. That is, unless obviously incompatible or specifically excluded, each individual embodiment is deemed to be combinable with any other embodiment(s) and the combination is considered to represent another distinct embodiment. Conversely, various features of the present disclosure that are described in the context of a single embodiment for brevity's sake may also be provided separately or in any sub-combination. Finally, while a particular embodiment may be described as part of a series of steps or part of a more general structure, each step or sub-structure may also be considered an independent embodiment in itself.

Unless stated otherwise, it is to be understood that each individual element in a list and every combination of individual elements in that list is to be interpreted as a distinct embodiment. For example, a list of embodiments presented as "A, B, or C" is to be interpreted as including the embodiments "A," "B," "C," "A or B," "A or C," "B or C," or "A, B, or C."

In the present disclosure, the singular forms of the articles "a," "an," and "the" also include the corresponding plural references, and reference to a particular numerical value includes at least that particular value, unless the context clearly indicates otherwise. Thus, for example, reference to "a material" is a reference to at least one of such materials and equivalents thereof.

In general, use of the term "about" indicates approximations that can vary depending on the desired properties sought to be obtained by the disclosed subject matter and is to be interpreted in a context-dependent manner based on functionality. Accordingly, one having ordinary skill in the art will be able to interpret a degree of variance on a case-by-case basis. In some instances, the number of significant figures used when expressing a particular value may be a representative technique of determining the variance permitted by the term "about." In other cases, the gradations in a series of values may be used to determine the range of variance permitted by the term "about." Further, all ranges in the present disclosure are inclusive and combinable, and references to values stated in ranges include every value within that range.

As discussed above, energy storage systems that are operable on a large scale while maintaining high efficiency values can be extremely desirable. Flow batteries employing coordination complexes as active materials have generated significant interest in this regard. Coordination complexes containing at least one catecholate ligand can be especially desirable due to their favorable aqueous solubility, stability, and operating characteristics, among other factors. Although metal catecholate complexes containing unsubstituted catecholate ligands can have acceptable solubility to promote efficient operation of flow batteries, there is still room for improving operating performance. In particular, incorporating one or more substituted catecholate ligands bearing solubilizing groups into metal catecholate complexes can improve battery performance through enhancing solubility.

As used herein, the term "catechol" refers to a compound having an aromatic ring bearing hydroxyl groups on adjacent carbon atoms (i.e., 1,2-hydroxyl groups). Optional substitution can also be present in addition to the 1,2-hydroxyl groups. As used herein, the term "catecholate" refers to a substituted or unsubstituted catechol compound that is bound to a metal center via a metal-ligand bond. The optional substitution on catecholate ligands can serve a number of purposes such as, for example, altering the solubility characteristics and/or half-cell potentials of the metal complexes where they are present.

1,2,4-Trihydroxybenzene is an example of one substituted catechol compound that can provide enhanced solubility when incorporated in a metal coordination complex. For example, whereas titanium catecholate complexes bearing only unsubstituted catecholate ligands (e.g., NaKTi(CAT)$_3$; CAT=1,2-dihydroxybenzene) have a maximum aqueous solubility of about 1.2 M, corresponding coordination complexes bearing at least one 1,2,4-trihydroxybenzene ligand (e.g., NaKTi(CAT)$_2$(THB); THB=1,2,4-trihydroxybenzene) can have an increased aqueous solubility of about 1.6 M. This solubility difference can be significant for enhancing the performance of flow batteries, particularly for large-scale applications.

Unfortunately, 1,2,4-trihydroxybenzene is not presently available in sufficient quantities to synthesize the significant amounts of active materials needed in support of commercial flow battery operations. Moreover, present commercial prices (>$200 per kilogram) are far too expensive to be economically viable for large scale applications.

Another difficulty associated with utilizing metal catecholate complexes in commercial flow battery operations is the significant amounts of hydroquinone byproduct formed during industrial synthesis of catechol. Although hydroquinone has value as a commodity chemical in other industries, it presently does not have any intrinsic value in the flow battery field. For integrated processes that produce metal catecholate complexes from a parent catechol feedstock, the hydroquinone byproduct can represent a significant waste disposal issue at the scales needed for commercial flow battery operations.

The present inventors developed a rapid, inexpensive, and high-yield route through which hydroquinone can be readily transformed into 1,2,4-trihydroxybenzene in a concerted synthetic process, as discussed hereinbelow. Converting the hydroquinone byproduct into a high-value product solves a number of potential issues associated with commercial flow battery operations. First, inexpensively converting the hydroquinone byproduct into a high-value product solves the potential waste disposal issues encountered when using commercial catechol as a commodity ligand. Second, the 1,2,4-trihydroxybenzene product itself can be readily incorporated in metal catecholate complexes, thereby providing active materials having enhanced solubility compared to corresponding complexes bearing only unsubstituted catecholate ligands. Advantageously, metal coordination complexes bearing 1,2,4-trihydroxybenzene as a substituted catecholate ligand remain economically viable due to the ease through which hydroquinone can be transformed by the processes described herein.

More specifically, the present inventors discovered a three-step concerted synthetic process (see Scheme 1 below) through which hydroquinone can be transformed into 1,2,4-trihydroxybenzene with high yields in each step. The inventors identified suitable conditions leading to formation of negligible byproducts in each synthetic step, such that each synthetic step can be conducted with minimal workup and little to no purification to provide synthetic intermediates or final product of sufficient purity for use in subsequent steps or for incorporation in a metal catecholate complex, such as metal catecholate complexes suitable for incorporation in a flow battery.

In various embodiments, synthetic methods of the present disclosure can include oxidizing hydroquinone in a first reaction to form p-benzoquinone, converting the p-benzoquinone in a second reaction to form 1,2,4-triacetoxybenzene, deacetylating the 1,2,4-triacetoxybenzene in a third reaction to form 1,2,4-trihydroxybenzene, and isolating the 1,2,4-trihydroxybenezene after performing the first reaction, the second reaction and the third reaction consecutively. Scheme 1 below illustrates the general synthetic transformations involved in the methods of the present disclosure. Scheme 2 below illustrates one set of illustrative reaction conditions that can be used to transform hydroquinone into 1,2,4-trihydroxybenezene according to the present disclosure. Additional details are provided hereinbelow.

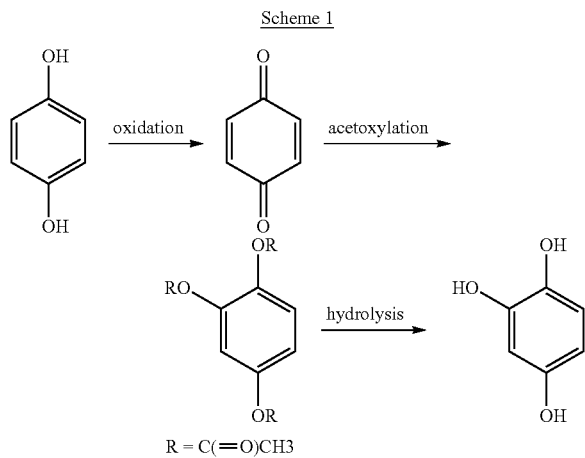

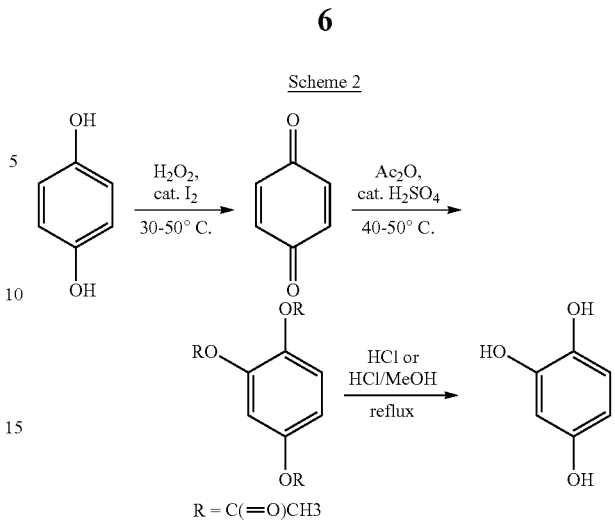

The hydroquinone can be obtained from any suitable source. In various embodiments, the hydroquinone can be sourced independently for conversion into the 1,2,4-trihydroxybenzene, or it can be obtained from a mixture of catechol and hydroquinone. Accordingly, in some embodiments, the methods of the present disclosure can further include obtaining the hydroquinone from a mixture of catechol and hydroquinone. In still further embodiments, the methods of the present disclosure can include separating the hydroquinone from the mixture before performing the series of reactions described herein. In other embodiments, the methods of the present disclosure can be practiced without separating the hydroquinone from the catechol before performing the series of reactions described herein. Catechol, for example, forms polymeric byproducts under Thiele-Winter acetoxylation conditions and can be separated from the 1,2,4-trihydroxybenzene product as such.

The methods described herein allow a concerted synthesis of 1,2,4-trihydroxybenzene to be realized from hydroquinone in consecutive synthetic transformations. The hydroquinone can be a byproduct from synthesis of catechol in some instances. In some embodiments, each of the first reaction, the second reaction and the third reaction can be performed with isolation and purification of the reaction product. In other embodiments, at least one of the first reaction and the second reaction can be performed without further purifying the p-benzoquinone or 1,2,4-triacetoxybenzene formed in the course of the first reaction or the second reaction. In some embodiments of the present disclosure, the first reaction and the second reaction can be performed such that the p-benzoquinone or 1,2,4-triacetoxybenzene precipitate from the reaction mixture and can be isolated by filtration. Under such reaction conditions, the p-benzoquinone and the 1,2,4-triacetoxybenzene can be isolated by filtration from the first reaction and the second reaction, respectively, but without otherwise further purifying before forming the 1,2,4-trihydroxybenzene in the third reaction.

Moreover, in some embodiments, the first reaction, the second reaction and the third reaction can be performed consecutively in a single reaction vessel (i.e., a one-pot synthesis). In other embodiments, the first reaction can be performed in a first reaction vessel, and the second and third reactions can be performed consecutively in a second reaction vessel (i.e., a two-pot synthesis). Isolation and optional purification of the p-benzoquinone can take place in such embodiments prior to the second reaction. In still other embodiments, isolation and optional purification of the p-benzoquinone can take place between the first reaction and the second reaction, and of the 1,2,4-triacetoxybenzene between the second reaction and the third reaction, such that the first reaction, the second reaction and the third reaction each take place independently in separate reaction vessels. In illustrative embodiments, the p-benzoquinone can be isolated from the first reaction by filtration, and/or the 1,2,4-triacetoxybenzene can be isolated from the second reaction by filtration. Additional details concerning particular reaction conditions under which filtration can be appropriate are provided hereinbelow.

In more particular embodiments, the first reaction can take place in a solvent in the presence of hydrogen peroxide and a catalytic amount of an iodine-containing substance, particularly molecular iodine. The hydrogen peroxide serves as a stoichiometric oxidant in such embodiments. Suitable iodine-containing substances can include, for example, molecular iodine (i.e., $I_2$), metal iodides (e.g., KI or NaI), or hydrogen iodide. Molecular iodine can be a particularly desirable iodine-containing substance for practicing the various methods described herein. Suitable solvents for the first reaction can include, but are not limited to, water, aqueous acids, alcohols (e.g., methanol, ethanol, propanol, isopropanol, or ethylene glycol), ethyl acetate, or any combination thereof. In order to facilitate the second reaction in some instances, particularly one-pot syntheses, it can be desirable to exclude water as a solvent in the first reaction. Isopropanol and ethyl acetate can be particularly desirable solvents for conducting the first reaction under the foregoing conditions.

In some embodiments, a suitable catalytic amount of the iodine-containing substance can range between about 0.001 to about 0.010 stoichiometric equivalents relative to hydroquinone. Larger amounts of the iodine-containing substance are also possible, and in more general embodiments, the catalytic amount of the iodine-containing substance can range between about 0.001 to about 0.1 stoichiometric equivalents relative to hydroquinone.

In some embodiments, a suitable amount of hydrogen peroxide can range between about 1.05 to about 1.5 stoichiometric equivalents relative to hydroquinone. In more specific embodiments, a suitable amount of hydrogen peroxide can range between about 1.1 to about 1.3 stoichiometric equivalents, or between about 1.15 to about 1.25 stoichiometric equivalents relative to hydroquinone.

The hydrogen peroxide utilized in the first reaction is not considered to be particularly limited in concentration. In general, between 3% to about 70% hydrogen peroxide by volume can be utilized. In some embodiments, 30% hydrogen peroxide or greater can be particularly desirable.

In some embodiments, a suitable temperature of the first reaction when utilizing hydrogen peroxide as the stoichiometric oxidant and molecular iodine in a catalytic amount can range between about 30° C. to about 50° C., or between about 35° C. to about 45° C.

In general, the acetoxylation taking place in the second reaction can occur under Thiele-Winter acetoxylation conditions. Accordingly, in some embodiments, the second reaction can take place in the presence of acetic anhydride and a catalytic amount of an acid. In some embodiments, the acid present in the catalytic amount in the second reaction can be sulfuric acid. Boron trifluoride diethyl etherate, perchloric acid, and trifluoromethanesulfonic acid can also be suitable catalytic acids in the second reaction in some embodiments. In still further embodiments, the second reaction can take place in the presence of acetic anhydride, a catalytic amount of acid (e.g., sulfuric acid), and added acetic acid. Under the foregoing reaction conditions, 1,2,4-triacetoxybenzene can precipitate from the reaction mixture in the second reaction. Accordingly, in some embodiments, methods of the present disclosure can include isolating the 1,2,4-triacetoxybenzene from the second reaction by filtration.

Various regioisomers can be formed during the acetoxylation of benzoquinone. The inventors discovered reaction conditions that minimize formation of minor product regioisomers. In various embodiments, the conditions of the second reaction can be tailored such that 1,2,4-triacetoxybenzene is the predominant product. Various conditions that can be varied to affect the outcome of the acetoxylation reaction are considered hereinafter. In more specific embodiments, conditions of the second reaction can be tailored such that amounts of 1,4-diacetoxybenzene and/or 1,2,4,5-tetraacetoxybenzene formed in the second reaction are independently less than about 0.5%. In more specific embodiments, the conditions of the second reaction can be tailored such that an amount of 1,4-diacetoxybenzene formed is less than about 0.3%, or less than about 0.2%, or less than about 0.1%. 1,2,4,5-tetraacetoxybenzene can also be formed under forcing conditions that can also favor the formation of 1,4-diacetoxybenzene. In such instances, higher quantities of 1,2,4,5-tetraacetoxybenzene can be formed, which can produce 1,2,4,5-tetrahydroxybenzene as another high-value product, if desired. Unreacted hydroquinone from the first reaction can also lead to formation of 1,4-diacetoxybenzene in the second reaction in some instances. Accordingly, high-yield conversion in the first reaction can be desirable. Minimizing the formation of 1,4-diacetoxybenzene and 1,2,4,5-tetraacetoxybenzene byproducts in the second reaction can leave the desired 1,2,4-trihydroxybenzene end product with suitable purity for use in downstream applications, such as forming a metal coordination complex for use in a flow battery. Without minimizing the formation of 1,4-diacetoxybenzene and 1,2,4,5-tetraacetoxybenzene byproducts, unwanted purification operations may be needed to make the 1,2,4-trihydroxybenzene suitable for further use, possibly compromising the economic viability of the synthetic methods described herein. As mentioned above, formation of 1,2,4,5-tetraacetoxybenzene and 1,2,4,5-tetrahydroxybenzene can also be a desirable outcome in some instances.

In some embodiments, a suitable catalytic amount of the acid in the second reaction can range between about 0.01 to about 0.5 stoichiometric equivalents relative to p-benzoquinone. In more particular embodiments, the catalytic amount of the acid used in the second reaction can range between about 0.05 to about 0.4 stoichiometric equivalents relative to p-benzoquinone, or between about 0.1 to about 0.3 stoichiometric equivalents relative to p-benzoquinone. In more specific embodiments, the acid utilized in the second reaction can be sulfuric acid, although other acids can also be suitable in some instances.

The amount of acetic anhydride used in the second reaction is generally present in at least a stoichiometric amount sufficient to introduce three acetoxy groups into p-benzoquinone. In some embodiments, the amount of acetic anhydride in the second reaction can range between about 2 to about 10 stoichiometric equivalents relative to p-benzoquinone. In more particular embodiments, the amount of acetic anhydride used in the second reaction can range between about 2 and about 3 stoichiometric equivalents relative to p-benzoquinone, or between about 2.2 and about 2.5 stoichiometric equivalents relative to p-benzoquinone.

In further embodiments, the second reaction can take place in the presence of acetic anhydride, the catalytic amount of the acid, and acetic acid. In more specific embodiments, the second reaction can take place in the presence of acetic anhydride, a catalytic amount of sulfuric acid, and acetic acid. The acetic anhydride and sulfuric acid can be present in the amounts noted above. When present, the amount of acetic acid can range between about 0.5 to about 5 stoichiometric equivalents relative to p-benzoquinone. In more particular embodiments, the amount of acetic acid in the second reaction can range between about 1 to about 3 stoichiometric equivalents relative to p-benzoquinone.

In some embodiments, the p-benzoquinone can be added to a mixture of acetic anhydride and sulfuric acid when conducting the second reaction. Addition of the p-benzoquinone to a mixture of acetic anhydride and sulfuric acid can be sufficiently exothermic such that that no external heat source is necessary to drive the second reaction. In some embodiments, the p-benzoquinone can be added to the mixture of acetic anhydride and the catalytic acid at a rate sufficient to maintain a temperature of the second reaction between about 30° C. to about 65° C. In more particular embodiments, the p-benzoquinone can be added to the mixture of acetic anhydride and the catalytic acid at a rate sufficient to maintain a temperature of the second reaction between about 30° C. to about 50° C., or between about 40° C. to about 50° C., or between about 30° C. to about 40° C. In other more particular embodiments, the p-benzoquinone can be added at a rate sufficient to maintain a temperature of the second reaction between about 55° C. and about 65° C.

When conducting the first reaction, the second reaction, and the third reaction consecutively in a single reaction vessel, acetic anhydride and the catalytic acid can be added to a mixture of p-benzoquinone, solvent and reagents from the first reaction. Alternately, a mixture of p-benzoquinone, solvent and reagents from the first reaction can be transferred without further purification to a mixture of acetic anhydride and catalytic acid in a second reaction vessel. Still further alternately, a mixture of p-benzoquinone, solvent and reagents from the first reaction can be transferred to a holding vessel, and a mixture of acetic anhydride and catalytic acid can be established in the first reaction vessel upon removal of the p-benzoquinone. Subsequently, the mixture of p-benzoquinone, solvent and reagents can be returned from the holding vessel to the mixture of acetic anhydride and catalytic acid.

In some embodiments, the third reaction can take place in the presence of hydrochloric acid or a mixture of hydrochloric acid and an alcohol, such as methanol. Under either set of reaction conditions, acid alcoholysis (trans-esterification) of the acetoxy groups can take place to yield 1,2,4-trihydroxybenzene as a reaction product. Heating can desirably accelerate the acid alcoholysis process in some embodiments. In some embodiments, the third reaction can be heated at the reflux temperature of the particular mixture of reagents used.

In alternative embodiments, the third reaction can take place in the presence of sulfuric acid and an alcohol, such as methanol, or in the presence of anhydrous HCl in an alcohol solvent. When sulfuric acid is present, $CaCl_2$ can be used to neutralize affect quenching of the acid by forming insoluble $CaSO_4$.

In some embodiments, the amount of hydrochloric acid or an equivalent acid used in the third reaction can be a catalytic amount with respect to the 1,2,4-triacetoxybenzene. For example, in some embodiments, the hydrochloric acid can be present in about 0.05 to about 0.5 stoichiometric equivalents with respect to 1,2,4-triacetoxybenzene, or about 0.1 to about 0.2 stoichiometric equivalents with respect to 1,2,4-triacetoxybenzene.

In still further embodiments, methods of the present disclosure can include forming a coordination complex containing 1,2,4-trihydroxybenzene as at least one ligand. In some embodiments, such coordination complexes containing 1,2,4-trihydroxybenzene as a ligand can also include at least one other catecholate ligand, such as an unsubstituted catecholate ligand.

Coordination complexes containing at least one 1,2,4-trihydroxybenzene ligand can contain a metal center to which the 1,2,4-trihydroxybenzene is coordinated. Such coordination complexes can be incorporated as at least one active material in a flow battery. Illustrative disclosure regarding flow batteries is provided hereinbelow. In more specific embodiments, coordination complexes containing a titanium center can be particularly desirable for incorporation in a flow battery. Other suitable metals are discussed hereinbelow.

Suitable conditions for forming coordination complexes containing 1,2,4-trihydroxybenzene and optionally other catecholate ligands will be familiar to one having ordinary skill in the art. In the discussion that follows, exemplary conditions for synthesizing titanium complexes will be provided in brief. It is to be recognized, however, that similar reaction conditions can be used to synthesize coordination complexes containing other metal centers using related methods. In various embodiments, suitable conditions for synthesizing titanium complexes can include, for example, reacting 1,2,4-trihydroxybenzene and other optional catecholate ligands with a titanium source such as titanium tetrachloride, titanium isopropoxide, or titanium oxychloride.

Accordingly, in some embodiments, coordination complexes of the present disclosure can have a formula of

$$D_gML_1L_2L_3,$$

in which D is H, ammonium, an alkali metal, or any combination thereof; g ranges between 0 and 6; M is a transition metal, and $L_1$, $L_2$ and $L_3$ are ligands, with at least one of and $L_1$, $L_2$ and $L_3$ being a 1,2,4-trihydroxybenzene ligand. In some embodiments, any of $L_1$, $L_2$ and $L_3$ that are not a 1,2,4-trihydroxybenzene ligand can be an unsubstituted catecholate ligand. Alternative ligands that can constitute the balance of $L_1$-$L_3$, optionally in combination with an unsubstituted or substituted catecholate ligand, include, but are not limited to, exemplary ligands described in further detail hereinbelow.

In more specific embodiments, D can be ammonium, an alkali metal, or any combination thereof, g can be 2, and M can be titanium. In still more specific embodiments, D can be a mixture of alkali metals, particularly a mixture of sodium and potassium. Accordingly, in embodiments wherein the metal center is titanium and a mixture of sodium and potassium counterions is present, the coordination complexes described herein can have a formula of

$$Na_mK_nTiL_1L_2L_3,$$

wherein m+n=2, provided that none of $L_1$-$L_3$ bear a charged functional group. For example, in the case of at least one of $L_1$-$L_3$ being a catecholate ligand bearing a negatively charged functional group (e.g., a sulfonic acid anion), greater than two molar equivalents of sodium and/or potassium ions are needed to maintain charge balance. In more particular embodiments, both m and n are non-zero numbers, and they can be equal or non-equal to one another. In some embodiments, a ratio of m to n can range between about 1:10 to about 10:1, or between about 1:5 or about 5:1. In some embodiments, substantially equal molar quantities of sodium and potassium can be present in the coordination complexes described herein.

In some embodiments, ligands other than substituted or unsubstituted catecholate ligands can be co-present with 1,2,4-trihydroxybenzene ligands in the coordination complexes described herein. Other ligands that can be present in in the complexes described herein include, for example, ascorbate, citrate, glycolate, a polyol, gluconate, hydroxyalkanoate, acetate, formate, benzoate, malate, maleate, phthalate, sarcosinate, salicylate, oxalate, urea, polyamine, aminophenolate, acetylacetonate, and lactate. Where chemically feasible, it is to be recognized that such ligands can be optionally substituted with at least one group selected from among $C_{1-6}$ alkoxy, $C_{1-6}$ alkyl, $C_{1-6}$ alkenyl, $C_{1-6}$ alkynyl, 5- or 6-membered aryl or heteroaryl groups, a boronic acid or a derivative thereof, a carboxylic acid or a derivative thereof, cyano, halide, hydroxyl, nitro, sulfonate, a sulfonic acid or a derivative thereof, a phosphonate, a phosphonic acid or a derivative thereof, or a glycol, such as polyethylene glycol. Alkanoate includes any of the alpha, beta, and gamma forms of these ligands. Polyamines include, but are not limited to, ethylenediamine, ethylenediamine tetraacetic acid (EDTA), and diethylenetriamine pentaacetic acid (DTPA).

Other examples of ligands that can be present in the complexes of the present disclosure can include monodentate, bidentate, and/or tridentate ligands. Examples of monodentate ligands that can be present in the complexes of the present disclosure include, for example, carbonyl or carbon monoxide, nitride, oxo, hydroxo, water, sulfide, thiols, pyridine, pyrazine, and the like. Examples of bidentate ligands that can be present in the complexes of the present disclosure include, for example, bipyridine, bipyrazine, ethylenediamine, diols (including ethylene glycol), and the like. Examples of tridentate ligands that can be present in the complexes of the present disclosure include, for example, terpyridine, diethylenetriamine, triazacyclononane, tris(hydroxymethyl)aminomethane, and the like.

In some embodiments, methods of the present disclosure can include forming an aqueous solution of a coordination complex containing 1,2,4-trihydroxybenzene as at least one ligand. In some embodiments, the aqueous solution can have a concentration of the coordination complex of about 0.5 M or above. In more particular embodiments, the aqueous solution can have a concentration of the coordination complex of about 0.5 M to about 2 M, or about 0.75 M to about 1.5 M, or about 1 M to about 2 M. For example, in the case of a titanium complex containing one 1,2,4-trihydroxybenzene ligand and two unsubstituted catecholate ligands, the aqueous solubility can be about 1.6 M.

In some embodiments, the aqueous solution can be substantially free of an organic solvent. In other embodiments, the aqueous solution can contain at least some organic solvent. In more particular embodiments, alcohol or glycol solvents can be present in the aqueous solution. In some embodiments, the aqueous solution can contain at least about 98% water by weight. In other embodiments, the aqueous solution can contain at least about 55% water by weight, or at least about 60% water by weight, or at least about 65% water by weight, or at least about 70% water by weight, or at least about 75% water by weight, or at least about 80% water by weight, or at least about 85% water by weight, or at least about 90% water by weight, or at least about 95% water by weight. In some embodiments, the aqueous solution can be free of water-miscible organic solvents and consist of water alone as a solvent.

In further embodiments, the aqueous solution can include a viscosity modifier, a wetting agent, a buffer, or any combination thereof. Suitable viscosity modifiers can include, for example, corn starch, corn syrup, gelatin, glycerol, guar gum, pectin, and the like. Other suitable examples will be familiar to one having ordinary skill in the art. Suitable wetting agents can include, for example, various non-ionic surfactants and/or detergents. In some or other embodiments, the aqueous solution can further include a glycol or a polyol. Suitable glycols can include, for example, ethylene glycol, diethylene glycol, and polyethylene glycol. Suitable polyols can include, for example, glycerol, mannitol, sorbitol, pentaerythritol, and tris(hydroxymethyl)aminomethane. Illustrative buffers that can be present include, but are not limited to, salts of phosphates, borates, carbonates, silicates, tris(hydroxymethyl)aminomethane (TRIS), 4-(2-hydroxyethyl)-1-piperazineethanesulfonic acid (HEPES), piperazine-N,N'-bis(ethanesulfonic acid) (PIPES), or any combination thereof. Inclusion of any of these components in the aqueous solution can help maintain the coordination complex in a dissolved form and/or facilitate the incorporation of the aqueous solution in a flow battery, for example.

In some embodiments, the aqueous solution can further include one or more mobile ions (i.e., an extraneous electrolyte) for use as an electrolyte solution in a flow battery or similar electrochemical system. In some embodiments, suitable mobile ions can include proton, hydronium, or hydroxide. In other various embodiments, mobile ions other than proton, hydronium, or hydroxide can be present, either alone or in combination with proton, hydronium or hydroxide. Such alternative mobile ions can include, for example, alkali metal or alkaline earth metal cations (e.g., $Li^+$, $Na^+$, $K^+$, $Mg^{2+}$, $Ca^{2+}$ and $Sr^{2+}$) and halides (e.g., $F^-$, $Cl^-$, or $Br^-$). Other suitable mobile ions can include, for example, ammonium and tetraalkylammonium ions, chalcogenides, phosphate, hydrogen phosphate, phosphonate, nitrate, sulfate, nitrite, sulfite, perchlorate, tetrafluoroborate, hexafluorophosphate, and any combination thereof. In some embodiments, less than about 50% of the mobile ions can constitute protons, hydronium, or hydroxide. In other various embodiments, less than about 40%, less than about 30%, less than about 20%, less than about 10%, less than about 5%, or less than about 2% of the mobile ions can constitute protons, hydronium, or hydroxide. In other various embodiments, the aqueous solution containing the coordination complex can lack an extraneous electrolyte altogether.

As indicated above, the coordination complexes of the present disclosure and related aqueous solutions containing these complexes can be incorporated in flow batteries and related electrochemical systems. Further disclosure on illustrative flow batteries and their operating parameters follows hereinafter.

In various embodiments, flow batteries of the present disclosure can include a first half-cell having a first electrolyte solution therein, in which the first electrolyte solution includes a coordination complex containing 1,2,4-trihydroxybenzene as a ligand. In some embodiments, the first electrolyte solution can be an aqueous solution, as defined above.

In further embodiments, flow batteries of the present disclosure can also include a second half-cell having a second electrolyte solution therein, where the second electrolyte solution contains an active material differing from that in the first electrolyte solution. In more specific embodiments, the second electrolyte solution can be an aqueous solution containing an iron hexacyanide complex. Iron hexacyanide complexes can be particularly desirable active materials due to their facile electrode kinetics and substantially reversible electrochemical behavior within the working electrochemical window of aqueous solutions. Hence, these complexes can allow high open circuit potentials and cell efficiencies to be realized, particularly in combination with a coordination complex containing 1,2,4-trihydroxybenzene as a ligand, more particularly a titanium coordination complex, in the first electrolyte solution. In more specific embodiments, flow batteries of the present disclosure can include the first electrolyte solution in contact with a negative electrode of the flow battery and the second electrolyte solution in contact with the positive electrode of the flow battery.

Illustrative flow battery configurations will now be described in further detail. The flow batteries of the present disclosure are, in some embodiments, suited to sustained charge or discharge cycles of several hour durations. As such, they can be used to smooth energy supply/demand profiles and provide a mechanism for stabilizing intermittent power generation assets (e.g., from renewable energy sources such as solar and wind energy). It should be appreciated, then, that various embodiments of the present disclosure include energy storage applications where such long charge or discharge durations are desirable. For example, in non-limiting examples, the flow batteries of the present disclosure can be connected to an electrical grid to allow renewables integration, peak load shifting, grid firming, baseload power generation and consumption, energy arbitrage, transmission and distribution asset deferral, weak grid support, frequency regulation, or any combination thereof. When not connected to an electrical grid, the flow batteries of the present disclosure can be used as power sources for remote camps, forward operating bases, off-grid telecommunications, remote sensors, the like, and any combination thereof. Further, while the disclosure herein is generally directed to flow batteries, it is to be appreciated that other electrochemical energy storage media can incorporate the aqueous phases described herein, specifically those utilizing stationary electrolyte solutions.

In some embodiments, flow batteries of the present disclosure can include: a first chamber containing a negative electrode contacting a first aqueous electrolyte solution; a second chamber containing a positive electrode contacting a second aqueous electrolyte solution, and a separator disposed between the first and second electrolyte solutions. The first aqueous electrolyte solution can include a coordination complex described hereinabove, particularly a titanium complex containing 1,2,4-trihydroxybenzene as at least one ligand. The chambers provide separate reservoirs within the cell, through which the first and/or second electrolyte solutions circulate so as to contact the respective electrodes and the separator. Each chamber and its associated electrode and electrolyte solution define a corresponding half-cell. The separator provides several functions which include, for example, (1) serving as a barrier to mixing of the first and second electrolyte solutions, (2) electrically insulating to reduce or prevent short circuits between the positive and negative electrodes, and (3) to facilitate ion transport between the positive and negative electrolyte chambers, thereby balancing electron transport during charge and discharge cycles. The negative and positive electrodes provide a surface where electrochemical reactions can take place during charge and discharge cycles. During a charge or discharge cycle, electrolyte solutions can be transported from separate storage tanks through the corresponding chambers. In a charging cycle, electrical power can be applied to the cell such that the active material contained in the second electrolyte solution undergoes a one or more electron oxidation and the active material in the first electrolyte solution undergoes a one or more electron reduction. Similarly, in a discharge cycle the second active material is reduced and the first active material is oxidized to generate electrical power.

In more specific embodiments, illustrative flow batteries of the present disclosure can include: (a) a first aqueous electrolyte solution containing a first coordination complex; (b) a second aqueous electrolyte solution containing a second coordination complex; (c) a separator positioned between said first and second aqueous electrolyte solutions; and (d) an optional mobile ion in the first and second aqueous electrolyte solutions. As described in more detail below, the separator can be an ionomer membrane, and it can have a thickness of less than 100 microns and have an associated net charge that is the same sign as that of the first and second coordination complexes.

FIG. 1 depicts a schematic of an illustrative flow battery. Unlike typical battery technologies (e.g., Li-ion, Ni-metal hydride, lead-acid, and the like), where active materials and other components are housed in a single assembly, flow batteries transport (e.g., via pumping) redox-active energy storage materials from storage tanks through an electrochemical stack. This design feature decouples the electrical energy storage system power from the energy storage capacity, thereby allowing for considerable design flexibility and cost optimization.

As shown in FIG. 1, flow battery system 1 includes an electrochemical cell that features separator 20 (e.g., a membrane) that separates the two electrodes 10 and 10' of the electrochemical cell. As used herein, the terms "separator" and "membrane" refer synonymously to an ionically conductive and electrically insulating material disposed between the positive and negative electrodes of an electrochemical cell. Electrodes 10 and 10' are formed from a suitably conductive material, such as a metal, carbon, graphite, and the like. Tank 50 contains first active material 30, which is capable of being cycled between an oxidized state and a reduced state.

Pump 60 affects transport of first active material 30 from tank 50 to the electrochemical cell. The flow battery also suitably includes second tank 50' that contains second active material 40. Second active material 40 can be the same material as active material 30, or it can be different. Second pump 60' can affect transport of second active material 40 to the electrochemical cell. Pumps can also be used to affect transport of the active materials from the electrochemical cell back to tanks 50 and 50' (not shown in FIG. 1). Other methods of affecting fluid transport, such as siphons, for example, can also suitably transport first and second active materials 30 and 40 into and out of the electrochemical cell. Also shown in FIG. 1 is power source or load 70, which completes the circuit of the electrochemical cell and allows a user to collect or store electricity during its operation.

It should be understood that FIG. 1 depicts a specific, non-limiting embodiment of a flow battery. Accordingly, flow batteries consistent with the spirit of the present disclosure can differ in various aspects relative to the configuration of FIG. 1. As one example, a flow battery system can include one or more active materials that are solids, gases, and/or gases dissolved in liquids. Active materials can be stored in a tank, in a vessel open to the atmosphere, or simply vented to the atmosphere.

The separator can be a porous membrane in some embodiments and/or an ionomer membrane in other various embodiments. In some embodiments, the separator can be formed from an ionically conductive polymer.

Polymer membranes can be anion- or cation-conducting electrolytes. Where described as an "ionomer," the terms refers to polymer membrane containing both electrically neutral repeating units and ionized repeating units, where the ionized repeating units are pendant and covalently bonded to the polymer backbone. In general, the fraction of ionized units can range from about 1 mole percent to about 90 mole percent. For example, in some embodiments, the content of ionized units is less than about 15 mole percent; and in other embodiments, the ionic content is higher, such as greater than about 80 mole percent. In still other embodiments, the ionic content is defined by an intermediate range, for example, in a range of about 15 to about 80 mole percent. Ionized repeating units in an ionomer can include anionic functional groups such as sulfonate, carboxylate, and the like. These functional groups can be charge balanced by, mono-, di-, or higher-valent cations, such as alkali or alkaline earth metals. Ionomers can also include polymer compositions containing attached or embedded quaternary ammonium, sulfonium, phosphazenium, and guanidinium residues or salts. Suitable examples will be familiar to one having ordinary skill in the art.

In some embodiments, polymers useful as a separator can include highly fluorinated or perfluorinated polymer backbones. Certain polymers useful in the present disclosure can include copolymers of tetrafluoroethylene and one or more fluorinated, acid-functional co-monomers, which are commercially available as NAFION™ perfluorinated polymer electrolytes from DuPont. Other useful perfluorinated polymers can include copolymers of tetrafluoroethylene and $FSO_2$—$CF_2CF_2CF_2CF_2$—O—CF=$CF_2$, FLEMION™ and SELEMION™.

Additionally, substantially non-fluorinated membranes that are modified with sulfonic acid groups (or cation exchanged sulfonate groups) can also be used. Such membranes can include those with substantially aromatic backbones such as, for example, polystyrene, polyphenylene, biphenyl sulfone (BPSH), or thermoplastics such as polyetherketones and polyethersulfones.

Battery-separator style porous membranes, can also be used as the separator. Because they contain no inherent ionic conduction capabilities, such membranes are typically impregnated with additives in order to function. These membranes typically contain a mixture of a polymer and inorganic filler, and open porosity. Suitable polymers can include, for example, high density polyethylene, polypropylene, polyvinylidene difluoride (PVDF), or polytetrafluoroethylene (PTFE). Suitable inorganic fillers can include silicon carbide matrix material, titanium dioxide, silicon dioxide, zinc phosphide, and ceria.

Separators can also be formed from polyesters, polyetherketones, poly(vinyl chloride), vinyl polymers, and substituted vinyl polymers. These can be used alone or in combination with any previously described polymer.

Porous separators are non-conductive membranes which allow charge transfer between two electrodes via open channels filled with electrolyte. The permeability increases the probability of chemicals (e.g., active materials) passing through the separator from one electrode to another and causing cross-contamination and/or reduction in cell energy efficiency. The degree of this cross-contamination can depend on, among other features, the size (the effective diameter and channel length), and character (hydrophobicity/hydrophilicity) of the pores, the nature of the electrolyte, and the degree of wetting between the pores and the electrolyte.

The pore size distribution of a porous separator is generally sufficient to substantially prevent the crossover of active materials between the two electrolyte solutions. Suitable porous membranes can have an average pore size distribution of between about 0.001 nm and 20 micrometers, more typically between about 0.001 nm and 100 nm. The size distribution of the pores in the porous membrane can be substantial. In other words, a porous membrane can contain a first plurality of pores with a very small diameter (approximately less than 1 nm) and a second plurality of pores with a very large diameter (approximately greater than 10 micrometers). The larger pore sizes can lead to a higher amount of active material crossover. The ability for a porous membrane to substantially prevent the crossover of active materials can depend on the relative difference in size between the average pore size and the active material. For example, when the active material is a metal center in a coordination complex, the average diameter of the coordination complex can be about 50% greater than the average pore size of the porous membrane. On the other hand, if a porous membrane has substantially uniform pore sizes, the average diameter of the coordination complex can be about 20% larger than the average pore size of the porous membrane. Likewise, the average diameter of a coordination complex is increased when it is further coordinated with at least one water molecule. The diameter of a coordination complex of at least one water molecule is generally considered to be the hydrodynamic diameter. In such embodiments, the hydrodynamic diameter is generally at least about 35% greater than the average pore size. When the average pore size is substantially uniform, the hydrodynamic radius can be about 10% greater than the average pore size.

In some embodiments, the separator can also include reinforcement materials for greater stability. Suitable reinforcement materials can include nylon, cotton, polyesters, crystalline silica, crystalline titania, amorphous silica, amorphous titania, rubber, asbestos, wood or any combination thereof.

Separators within the flow batteries of the present disclosure can have a membrane thickness of less than about 500 micrometers, or less than about 300 micrometers, or less than about 250 micrometers, or less than about 200 micrometers, or less than about 100 micrometers, or less than about 75 micrometers, or less than about 50 micrometers, or less than about 30 micrometers, or less than about 25 micrometers, or less than about 20 micrometers, or less than about 15 micrometers, or less than about 10 micrometers. Suitable separators can include those in which the flow battery is capable of operating with a current efficiency of greater than about 85% with a current density of 100 mA/cm$^2$ when the separator has a thickness of 100 micrometers. In further embodiments, the flow battery is capable of operating at a current efficiency of greater than 99.5% when the separator has a thickness of less than about 50 micrometers, a current efficiency of greater than 99% when the separator has a thickness of less than about 25 micrometers, and a current efficiency of greater than 98% when the separator has a thickness of less than about 10 micrometers. Accordingly, suitable separators include those in which the flow battery is capable of operating at a voltage efficiency of greater than 60% with a current density of 100 mA/cm$^2$. In further embodiments, suitable separators can include those in which the flow battery is capable of operating at a voltage efficiency of greater than 70%, greater than 80% or even greater than 90%.

The diffusion rate of the first and second active materials through the separator can be less than about $1\times10^{-5}$ mol cm$^{-2}$ day$^{-1}$, or less than about $1\times10^{-6}$ mol cm$^{-2}$ day$^{-1}$, or less than about $1\times10^{-7}$ mol cm$^{-2}$ day$^{-1}$, or less than about $1\times10^{-9}$ mol cm$^{-2}$ day$^{-1}$, or less than about $1\times10^{-11}$ mol cm$^{-2}$ day$^{-1}$, or less than about $1\times10^{-13}$ mol cm$^{-2}$ day$^{-1}$, or less than about $1\times10^{-15}$ mol cm$^{-2}$ day$^{-1}$.

The flow batteries can also include an external electrical circuit in electrical communication with the first and second electrodes. The circuit can charge and discharge the flow battery during operation. Reference to the sign of the net ionic charge of the first, second, or both active materials relates to the sign of the net ionic charge in both oxidized and reduced forms of the redox active materials under the conditions of the operating flow battery. Further exemplary embodiments of a flow battery provide that (a) the first active material has an associated net positive or negative charge and is capable of providing an oxidized or reduced form over an electric potential in a range of the negative operating potential of the system, such that the resulting oxidized or reduced form of the first active material has the same charge sign (positive or negative) as the first active material and the ionomer membrane also has a net ionic charge of the same sign; and (b) the second active material has an associated net positive or negative charge and is capable of providing an oxidized or reduced form over an electric potential in a range of the positive operating potential of the system, such that the resulting oxidized or reduced form of the second active material has the same charge sign (positive or negative sign) as the second active material and the ionomer membrane also has a net ionic charge of the same sign; or both (a) and (b). In some embodiments, the net ionic charge in both the oxidized and reduced forms can be negative. The matching charges of the first and/or second active materials and the ionomer membrane can provide a high selectivity. More specifically, charge matching can provide less than about 3%, less than about 2%, less than about 1%, less than about 0.5%, less than about 0.2%, or less than about 0.1% of the molar flux of ions passing through the ionomer membrane as being attributable to the first or second active material. The term "molar flux of ions" will refer to the amount of ions passing through the ionomer membrane, balancing the charge associated with the flow of external electricity/electrons. That is, the flow battery is capable of operating or operates with the substantial exclusion of the active materials by the ionomer membrane, and such exclusion can be promoted through charge matching.

Flow batteries incorporating the electrolyte solutions of the present disclosure can have one or more of the following operating characteristics: (a) where, during the operation of the flow battery, the first or second active materials comprise less than about 3% of the molar flux of ions passing through the ionomer membrane; (b) where the round trip current efficiency is greater than about 70%, greater than about 80%, or greater than about 90%; (c) where the round trip current efficiency is greater than about 90%; (d) where the sign of the net ionic charge of the first, second, or both active materials is the same in both oxidized and reduced forms of the active materials and matches that of the ionomer membrane; (e) where the ionomer membrane has a thickness of less than about 100 µm, less than about 75 µm, less than about 50 µm, or less than about 250 µm; (f) where the flow battery is capable of operating at a current density of greater than about 100 mA/cm$^2$ with a round trip voltage efficiency of greater than about 60%; and (g) where the energy density of the electrolyte solutions is greater than about 10 Wh/L, greater than about 20 Wh/L, or greater than about 30 Wh/L.

In some cases, a user may desire to provide higher charge or discharge voltages than available from a single battery cell. In such cases, several battery cells can be connected in series such that the voltage of each cell is additive. This forms a bipolar stack. An electrically conductive, but non-porous material (e.g., a bipolar plate) can be employed to connect adjacent battery cells in a bipolar stack, which allows for electron transport but prevents fluid or gas transport between adjacent cells. The positive electrode compartments and negative electrode compartments of individual cells can be fluidically connected via common positive and negative fluid manifolds in the stack. In this way, individual cells can be stacked in series to yield a voltage appropriate for DC applications or conversion to AC applications.

In additional embodiments, the cells, cell stacks, or batteries can be incorporated into larger energy storage systems, suitably including piping and controls useful for operation of these large units. Piping, control, and other equipment suitable for such systems are known in the art, and can include, for example, piping and pumps in fluid communication with the respective chambers for moving electrolyte solutions into and out of the respective chambers and storage tanks for holding charged and discharged electrolytes. The cells, cell stacks, and batteries of this disclosure can also include an operation management system. The operation management system can be any suitable controller device, such as a computer or microprocessor, and can contain logic circuitry that sets operation of any of the various valves, pumps, circulation loops, and the like.

In more specific embodiments, a flow battery system can include a flow battery (including a cell or cell stack); storage tanks and piping for containing and transporting the electrolyte solutions; control hardware and software (which may include safety systems); and a power conditioning unit. The flow battery cell stack accomplishes the conversion of charging and discharging cycles and determines the peak power. The storage tanks contain the positive and negative active materials, such as the coordination complexes disclose herein, and the tank volume determines the quantity of energy stored in the system. The control software, hardware, and optional safety systems suitably include sensors, mitigation equipment and other electronic/hardware controls and safeguards to ensure safe, autonomous, and efficient operation of the flow battery system. A power conditioning unit can be used at the front end of the energy storage system to convert incoming and outgoing power to a voltage and current that is optimal for the energy storage system or the application. For the example of an energy storage system connected to an electrical grid, in a charging cycle the power conditioning unit can convert incoming AC electricity into DC electricity at an appropriate voltage and current for the cell stack. In a discharging cycle, the stack produces DC electrical power and the power conditioning unit converts it to AC electrical power at the appropriate voltage and frequency for grid applications.

Where not otherwise defined hereinabove or understood by one having ordinary skill in the art, the definitions in the following paragraphs will be applicable to the present disclosure.

As used herein, the term "energy density" will refer to the amount of energy that can be stored, per unit volume, in the active materials. Energy density refers to the theoretical energy density of energy storage and can be calculated by Equation 1:

$$\text{Energy density} = (26.8 \text{ A-h/mol}) \times \text{OCV} \times [e^-] \quad (1)$$

where OCV is the open circuit potential at 50% state of charge, (26.8 A-h/mol) is Faraday's constant, and $[e^-]$ is the concentration of electrons stored in the active material at 99% state of charge. In the case that the active materials largely are an atomic or molecular species for both the positive and negative electrolyte, $[e^-]$ can be calculated by Equation 2 as:

$$[e^-] = [\text{active materials}] \times N/2 \quad (2)$$

where [active materials] is the molar concentration of the active material in either the negative or positive electrolyte, whichever is lower, and N is the number of electrons transferred per molecule of active material. The related term "charge density" will refer to the total amount of charge that each electrolyte contains. For a given electrolyte, the charge density can be calculated by Equation 3

$$\text{Charge density} = (26.8 \text{ A-h/mol}) \times [\text{active material}] \times N \quad (3)$$

where [active material] and N are as defined above.

As used herein, the term "current density" will refer to the total current passed in an electrochemical cell divided by the geometric area of the electrodes of the cell and is commonly reported in units of mA/cm$^2$.

As used herein, the term "current efficiency" ($I_{eff}$) can be described as the ratio of the total charge produced upon discharge of a cell to the total charge passed during charging. The current efficiency can be a function of the state of charge of the flow battery. In some non-limiting embodiments, the current efficiency can be evaluated over a state of charge range of about 35% to about 60%.

As used herein, the term "voltage efficiency" can be described as the ratio of the observed electrode potential, at a given current density, to the half-cell potential for that electrode (×100%). Voltage efficiencies can be described for a battery charging step, a discharging step, or a "round trip voltage efficiency." The round trip voltage efficiency ($V_{eff,rt}$) at a given current density can be calculated from the cell voltage at discharge ($V_{discharge}$) and the voltage at charge ($V_{charge}$) using equation 4:

$$V_{eff,RT} = V_{discharge}/V_{charge} \times 100\% \quad (4)$$

As used herein, the terms "negative electrode" and "positive electrode" are electrodes defined with respect to one another, such that the negative electrode operates or is designed or intended to operate at a potential more negative than the positive electrode (and vice versa), independent of the actual potentials at which they operate, in both charging and discharging cycles. The negative electrode may or may not actually operate or be designed or intended to operate at a negative potential relative to a reversible hydrogen electrode. The negative electrode is associated with a first electrolyte solution and the positive electrode is associated with a second electrolyte solution, as described herein. The electrolyte solutions associated with the negative and positive electrodes may be described as negolytes and posolytes, respectively.

EXAMPLES

Example 1: Synthesis of p-Benzoquinone from Hydroquinone

Figure 2:
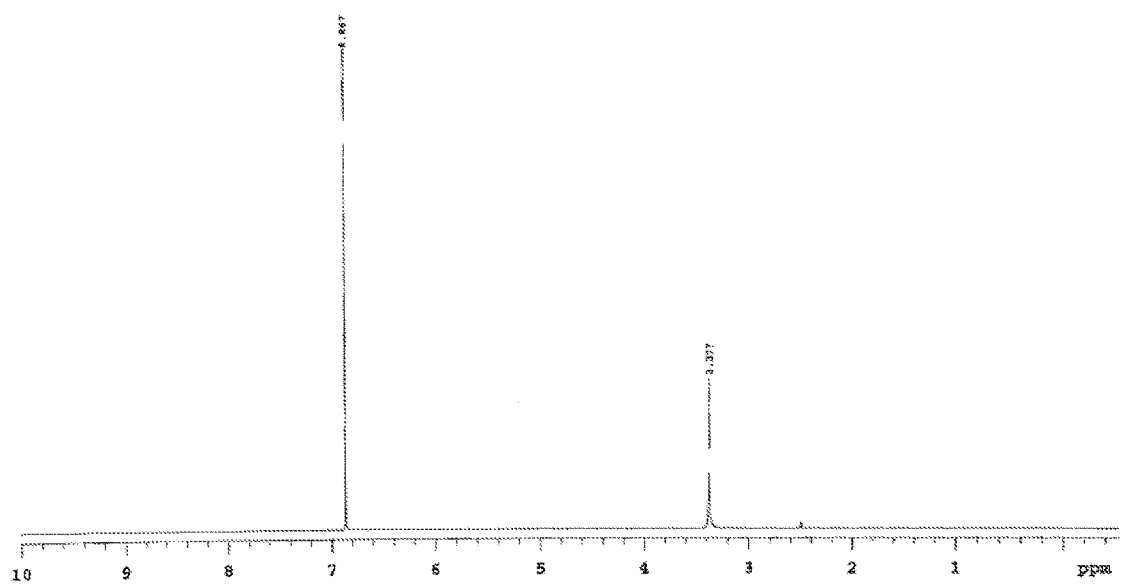
FIG. 2 shows an illustrative $^1$H NMR spectrum in DMSO-$d_6$ of p-benzoquinone synthesized by catalytic oxidation of hydroquinone in a 3% aqueous sulfuric acid solvent.

In an illustrative reaction, 55 g of hydroquinone (0.5 mol, 1 equivalent) and 1.0 g of iodine (0.0039 mol, 0.008 equivalents) were combined in 100-150 mL of a solvent (3% aqueous $H_2SO_4$, ethyl acetate, or isopropanol) to form a suspension. To the suspension was then added 62 mL of 30% aqueous hydrogen peroxide (0.6 mol, 1.2 equivalents) dropwise over 2-3 hours at a rate sufficient to maintain the reaction at 30-50° C. during the addition with no external heat being applied. A thick green slurry formed during addition of the hydrogen peroxide. The green solid is believed to be a p-benzoquinone-hydroquinone quinhydrone complex formed during the reaction. After addition of the hydrogen peroxide was complete, the reaction mixture was heated an additional 2-3 hours at 45° C., during which time the green solid was consumed, and a brown color formed. The reaction mixture was then cooled in an ice bath, filtered, and washed with cold solvent to produce substantially pure p-benzoquinone as a brown or yellow solid. The yield ranged from 71% to 82% depending on solvent. FIG. 2 shows an illustrative $^1$H NMR spectrum in DMSO-$d_6$ of p-benzoquinone synthesized by catalytic oxidation of hydroquinone in a 3% aqueous sulfuric acid solvent. The purity was >99.5% by GC. Up to about 0.3% hydroquinone remained by GC and was carried forward.

Example 2: Synthesis of 1,2,4-Triacetoxybenzene from p-Benzoquinone

Figure 3:
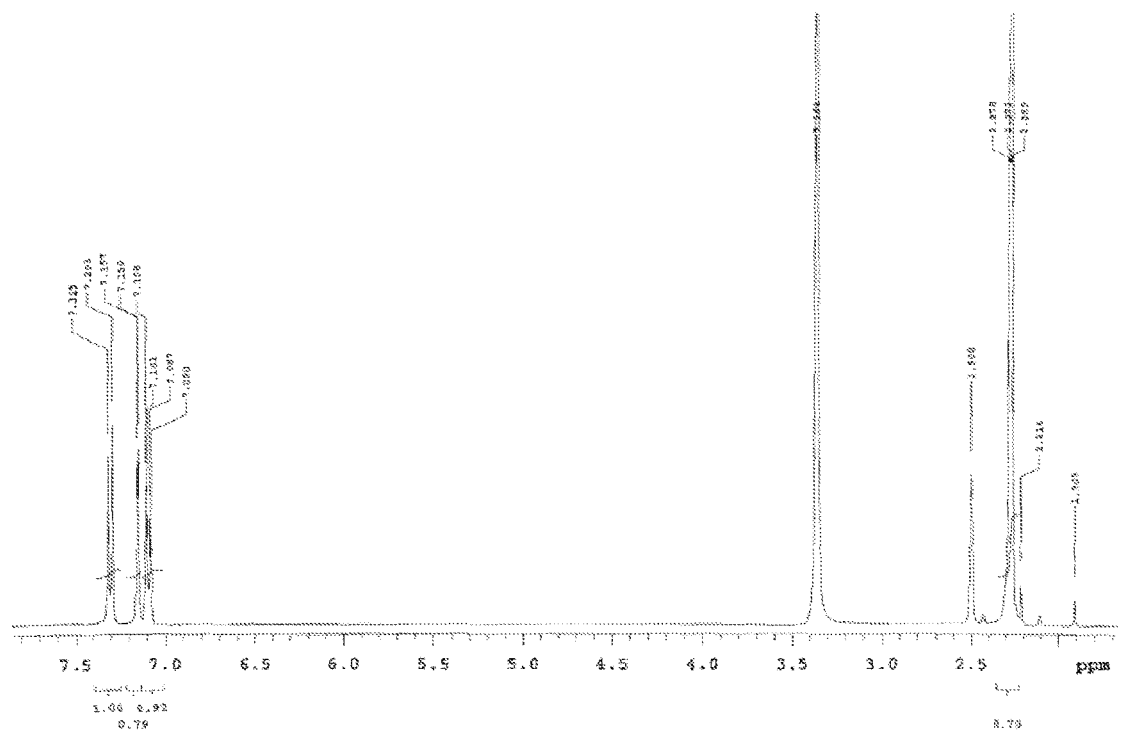
FIG. 3 shows an illustrative $^1$H NMR spectrum in DMSO-$d_6$ of 1,2,4-triacetoxybenzene synthesized by Thiele-Winter acetoxylation of p-benzoquinone.

In an illustrative reaction, 33 mL of sulfuric acid (0.612 mol, 0.22 equivalents) was added to 840 mL of acetic anhydride (8.88 mol, 3.2 equivalents) in a 5 L multi-neck roundbottom flask. To the acetic anhydride/sulfuric acid mixture was added 300 g of p-benzoquinone in portions with constant mechanical stirring. The reaction was exothermic, and the rate of addition was maintained such that the temperature ranged between 40° C. and 50° C. No external heat was applied during the addition process. After addition of the p-benzoquinone was complete, the reaction was allowed to cool to 25° C. (room temperature) over about 30 minutes. Solids formed in the roundbottom flask upon cooling. The contents of the flask were mixed with 6 L of ice water, and off-white solids formed. The solids were collected by filtration and washed with 14 L of water until the pH of the washings exceeded 5. After drying under vacuum, 671 g of off-white solid was collected (96%). FIG. 3 shows an illustrative $^1$H NMR spectrum in DMSO-$d_6$ of 1,2,4-triacetoxybenzene synthesized by Thiele-Winter acetoxylation of p-benzoquinone. The purity was 99.7% by GC. Additional details concerning optimization of the reaction conditions is provided in Example 4 below.

Figure 4:
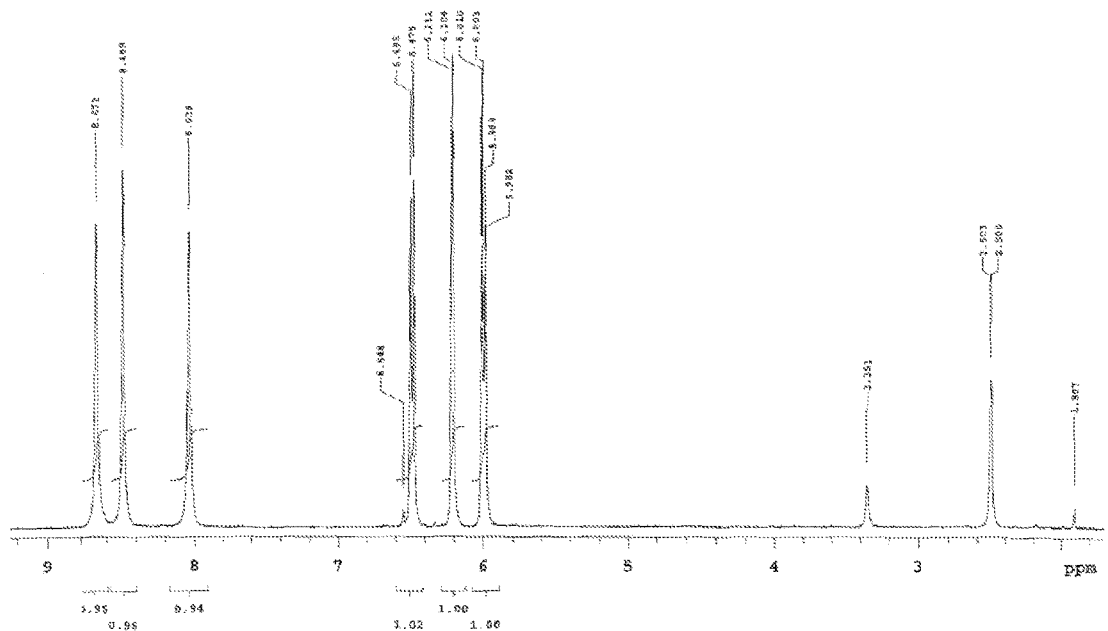
FIG. 4 shows an illustrative $^1$H NMR spectrum in DMSO-$d_6$ of 1,2,4-trihydroxybenzene synthesized by acidic hydrolysis of 1,2,4-triacetoxybenzene.

Example 3: Synthesis of 1,2,4-Trihydroxybenzene from 1,2,4-Triacetoxybenzene In an illustrative reaction, 670 g of 1,2,4-triacetoxybenzene (2.656 mol, 1 equivalent) was combined with 2.5 L of methanol, 1.5 L of deionized water, and 22 mL of 12 N hydrochloric acid (0.264 mol, 0.1 equivalents). The reaction mixture was then heated at reflux for 7 hours and cooled to room temperature over 14 hours. The reaction mixture was taken to dryness under reduced pressure to provide brown solids. 2 L of ethyl acetate was then added to the brown solids, which were then dissolved with heating. 200 g of solid NaHCO$_3$ and 20 g of activated charcoal were then added. After heating to boiling for 30 minutes, the ethyl acetate solution was then allowed to partially cool. When the temperature reached approximately 45° C., the solids were removed by filtration and washed with an additional 400 mL of ethyl acetate. The filtrate was taken to dryness under reduced pressure to provide the product as a pale orange solid. After drying under vacuum, 314 g of product was collected (98%). FIG. 4 shows an illustrative $^1$H NMR spectrum in DMSO-$d_6$ of 1,2,4-trihydroxybenzene synthesized by acidic hydrolysis of 1,2,4-triacetoxybenzene. Additional purification was realized through recrystallization from ethyl acetate in some instances.

Example 4: Optimization of the Synthesis of 1,2,4-Triacetoxybenzene from p-Benzoquinone Synthesis of 1,2,4-triacetoxybenzene was generally carried out as described above in Example 2 with the following additional modifications summarized below in Table 1.

lents of sulfuric acid at 40-45° C. Thereafter, 9.9 equivalents of acetic anhydride was added at a rate sufficient to maintain the temperature below 50° C. Heating was maintained at 45° C. for 22 hours.

3. Reaction to form 1,2,4-trihydroxybenzene. To the crude reaction mixture from the second step was added 21 equivalents of methanol at 45° C. After quenching of the excess acetic anhydride in an exothermic reaction, the reaction mixture was then heated to 60° C. Two additional portions of 9.9 equivalents of methanol each were added 5 and 6.5 hours later. After heating 15 hours, the reaction mixture was cooled and 0.05 equivalents of $K_2CO_3$ were added, followed by 0.35 equivalents of $KHCO_3$. The pH at this point was 4.33. The reaction mixture was filtered, and the filtrate was

| Entry | Acetic Anhydride (equiv.) | Acetic Acid (equiv.) | $H_2SO_4$ (equiv.) | Other | Yield (%) | GC Purity (%) | Yield Co-Product A (%) | Yield Co-Product B (%) |
|---|---|---|---|---|---|---|---|---|
| Ex. 2 | 3.2 | — | 0.22 | 40-50° C. | 96 | 99.7 | 0.15 | 0.17 |
| A | 3.2 | — | 0.2 | 1 equiv. $H_2O$, 40-50° C., additional 1 hr heat at 45° C. | 93 | 98 | ND | 0.3 |
| B | 2.2 | — | 0.22 | 40-50° C. | 93 | 99.2 | 0.8 | 0 |
| C | 3.2 | — | 0.10 | 40-50° C., then heat at 45° C. overnight | 91 | 99.1 | 0.42 | 0.52 |
| D | 2.2 | 1.0 | 0.22 | 40-50° C. | 92 | 99.8 | 0.20 | 0 |
| E | 2.5 | — | 0.22 | reaction temperature briefly reached 58° C. | ND | 95.3 | 0.16 | 0.33 |
| F | 2.8 | — | 0.20 | 40-50° C. | 95 | 98.9 | 0.34 | 0.26 |
| G | 2.2 | 2.0 | 0.22 | 40-50° C. | 96 | 99.7 | 0.30 | 0 |
| H | 2.2 | 3.0 | 0.22 | 40-50° C. | 90 | 99.3 | 0.52 | 0.14 |
| I | 2.2 | 2.0 | 0.10 | 40-50° C., $H_2SO_4$ addition started at 40° C. | 92 | 97.4 | 2.22 | 0.24 |
| J | 2.2 | 2.0 | 0.30 | 40-50° C. | ND | 99.5 | 0.30 | 0.07 |
| K | 2.2 | 2.0 | 0.22 | 55-65° C., stirred 2 hours after addition | 98 | 99.2 | 0.36 | 0.16 |
| L | 2.2 | 2.0 | 0.22 | 30-40° C., stirred 14 hours after addition | 95 | 99.7 | 0.09 | 0.08 |
| M | 2.2 | 2.0 | 1.0 | 40-50° C., other products account for balance of yield | ND | 31.7 | 40.0 | 0.1 |
| N | 2.2 | 2.0 | 0.22 | 25-30° C. | ND | 94.9 | 4.8 | 0.21 |

Co-Product A = 1,4-diacetoxybenzene
Co-Product B = 1,2,4,5-tetrahydroxybenzene

Example 5: One-Pot Synthesis of 1,2,4-Trihydroxybenzene from Hydroquinone

The reactions to form p-benzoquinone, 1,2,4-triacetoxybenzene, and 1,2,4-trihydroxybenzene were generally conducted as described above for Examples 1-3, except that isolation and purification were not conducted after the first and second synthetic steps. Additional changes to the starting reagents and reaction conditions were as follows:

1. Reaction to form p-benzoquinone: Ethyl acetate used as the solvent. The reaction was stirred at 45° C. for one hour and then overnight at room temperature. The resulting reaction mixture was red-brown and contained a suspended yellow solid.

Figure 5:
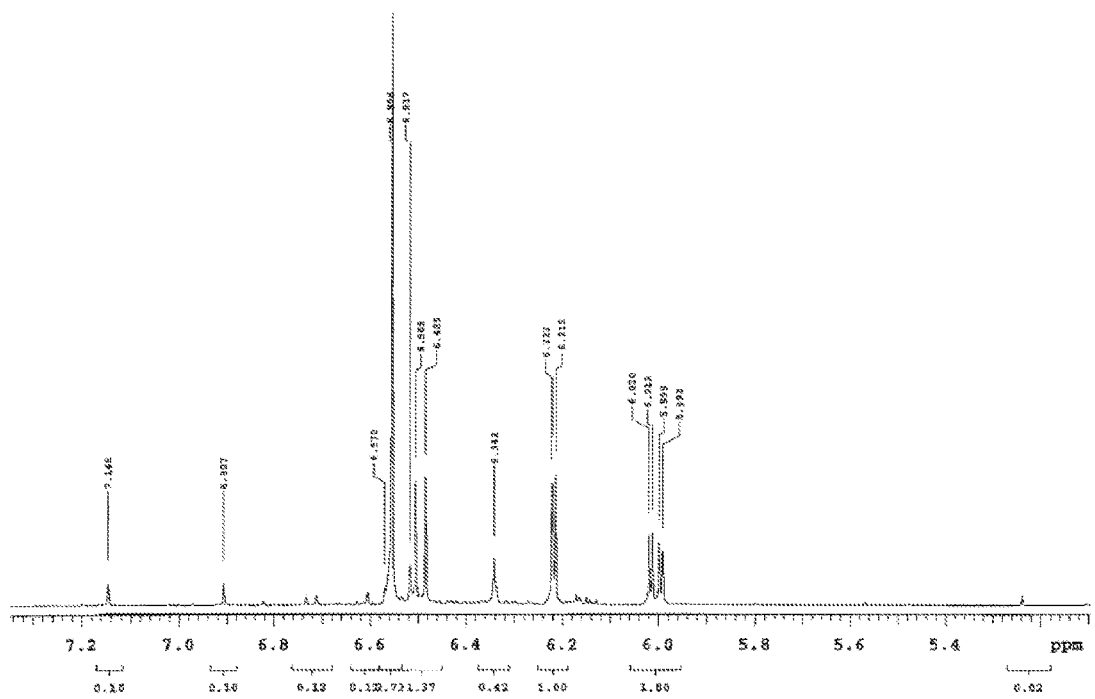
FIG. 5 shows an illustrative $^1$H NMR spectrum in DMSO-$d_6$ of crude 1,2,4-trihydroxybenzene obtained in a one-pot synthesis starting from hydroquinone.

2. Reaction to form 1,2,4-triacetoxybenzene: To the crude reaction mixture from the first step was added 0.1 equivareduced to a thick brown oil following removal of solvent under reduced pressure. FIG. 5 shows an illustrative $^1$H NMR spectrum in DMSO-$d_6$ of crude 1,2,4-trihydroxybenzene obtained in a one-pot synthesis starting from hydroquinone. Comparing FIG. 5 to FIG. 4, it can be seen that the desired 1,2,4-trihydroxybenzene product was produced in the one-pot reaction.

Figure 6:
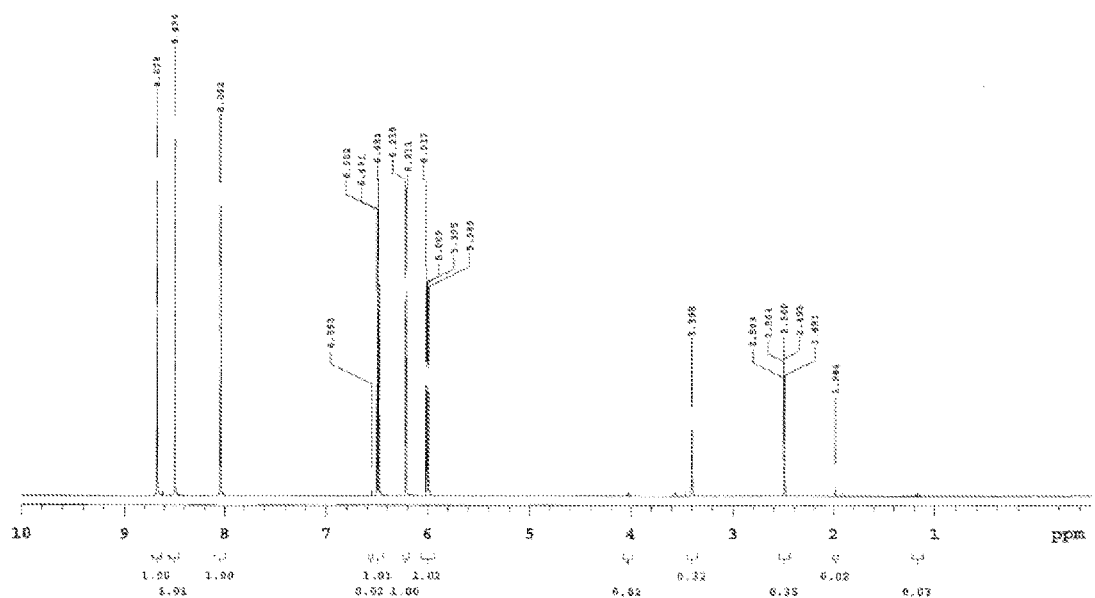
FIG. 6 shows an illustrative $^1$H NMR spectrum in DMSO-$d_6$ of crude 1,2,4-trihydroxybenzene obtained in a one-pot synthesis starting from p-benzoquinone.

Example 6: One-Pot Synthesis of 1,2,4-Trihydroxybenzene from p-Benzoquinone p-Benzoquinone was obtained as described in Example 1 above. 1,2,4-Triacetoxybenzene was formed as in Example 2 above, except 2.8 equivalents of acetic anhydride was used, and the reaction product was not separated following cooling to room temperature. After cooling the crude 1,2,4- triacetoxybenzene to room temperature, 11.2 equivalents of methanol was added, and the reaction mixture was heated at reflux for 1.5 hours. Following cooling to room temperature, 0.2 equivalents of CaCl$_2$ was added to the reaction mixture, which was then stirred for 40 minutes thereafter. The reaction mixture was then filtered, and the filtrate was concentrated under reduced pressure to provide a sticky purple solid. The purple solid was redissolved in hot ethyl acetate, and activated charcoal was then added and mixed for 30 minutes. The solution was filtered, partially concentrated under reduced pressure, and seeded with solid 1,2,4-trihydroxybenzene. After cooling at −20° C., a first crop of product was obtained as a white solid, and a second crop of product was obtained as a tan solid (overall yield=47%). FIG. 6 shows an illustrative $^1$H NMR spectrum in DMSO-d$_6$ of crude 1,2,4-trihydroxybenzene obtained in a one-pot synthesis starting from p-benzoquinone. Comparing FIG. 6 to FIG. 4, it can be seen that the desired 1,2,4-trihydroxybenzene product was produced in the one-pot reaction.

Although the disclosure has been described with reference to the disclosed embodiments, those skilled in the art will readily appreciate that these are only illustrative of the disclosure. It should be understood that various modifications can be made without departing from the spirit of the disclosure. The disclosure can be modified to incorporate any number of variations, alterations, substitutions or equivalent arrangements not heretofore described, but which are commensurate with the spirit and scope of the disclosure. Additionally, while various embodiments of the disclosure have been described, it is to be understood that aspects of the disclosure may include only some of the described embodiments. Accordingly, the disclosure is not to be seen as limited by the foregoing description.

What is claimed is the following:

1. A method of producing 1,2,4-trihydroxybenzene comprising the steps of:
    (a) mixing p-benzoquinone in the presence of:
        (i) at least two equivalents of acetic anhydride per equivalent of the p-benzoquinone, and
        (ii) a catalytic amount of an acid selected from the group consisting of sulfuric acid, boron trifluoride diethyl etherate, perchloric acid, and trifluoromethanesulfonic acid,
    under conditions sufficient to form a crude 1,2,4-triacetoxybenzene mixture comprising 1,2,4-triacetoxybenzene, acetic anhydride, acetic acid, and less than 0.5 mol % of 1,4-diacetoxybenzene relative to the initial p-benzoquinone;
    (b) combining the crude 1,2,4-triacetoxybenzene mixture with an excess alcohol sufficient to neutralize excess acetic anhydride in the absence of added water and the presence of an acid catalyst, and heating the resulting reaction mixture under conditions sufficient to form 1,2,4-trihydroxybenzene; and
    (c) isolating the 1,2,4-trihydroxybenzene.

2. The method of claim 1, wherein the 1,2,4-triacetoxybenzene is isolated from the crude 1,2,4-triacetoxybenzene mixture by filtration from step (a), but is otherwise used without further purification before forming the 1,2,4-trihydroxybenzene in step (b).

3. The method of claim 1, wherein the crude 1,2,4-triacetoxybenzene mixture contains less than 0.5 mol % of 1,2,4,5-tetraacetoxybenzene.

4. The method of claim 1, wherein steps (a) and (b) are performed consecutively in a single reaction vessel.

5. The method of claim 1, wherein step (a) is conducted in the presence of excess acetic anhydride and a catalytic amount of the acid.

6. The method of claim 5, wherein the acid is sulfuric acid.

7. The method of claim 5, wherein the p-benzoquinone is added to a mixture of acetic anhydride and the acid at a rate sufficient to maintain a temperature during step (b) between about 40° C. and about 50° C.

8. The method of claim 1, wherein the alcohol used in step (b) is methanol.

9. The method of claim 1, further comprising:
    reacting the 1,2,4-trihydroxybenzene from step (b) with a transition metal precursor to form a coordination complex having 1,2,4-trihydroxybenzene as at least one ligand.

10. The method of claim 9, wherein the coordination complex has a formula of

wherein D is H, ammonium, an alkali metal, or any combination thereof; g ranges between 0 and 6; M is a transition metal; and $L_1$, $L_2$ and $L_3$ are ligands, at least one of $L_1$, $L_2$ and $L_3$ is a 1,2,4-trihydroxybenzene ligand.

11. The method of claim 10, wherein D is ammonium, an alkali metal, or any combination thereof; g is 2; and M is Ti.

12. The method of claim 1, wherein the 1,4-diacetoxybenzene formed in step (a) is limited to an amount up to about 0.3%.

13. The method of claim 1, wherein the 1,4-diacetoxybenzene formed in step (a) is limited to an amount up to about 0.2%.

14. The method of claim 1, wherein the 1,4-diacetoxybenzene formed in step (a) is limited to an amount up to about 0.15%.

15. The method of claim 1, wherein step (a) is preceded by a step:
    (d) oxidizing hydroquinone to form a crude p-benzoquinone product mixture comprising p-benzoquinone.

16. The method of claim 15, wherein the oxidation of the hydroquinone is done in a solvent in the presence of hydrogen peroxide and a catalytic amount of a source of molecular iodine.

17. The method of claim 16, wherein the solvent is ethyl acetate, isopropanol, an aqueous acid, or any combination thereof.

18. The method of claim 16, wherein the solvent is an alcohol or ethyl acetate that is free from added water.

19. The method of claim 15, wherein the crude p-benzoquinone product mixture is used without further purification as the source of the p-benzoquinone in step (a).

* * * * *

UNITED STATES PATENT AND TRADEMARK OFFICE
CERTIFICATE OF CORRECTION

| | | |
|---|---|---|
| PATENT NO. | : 10,065,977 B2 | Page 1 of 5 |
| APPLICATION NO. | : 15/298175 | |
| DATED | : September 4, 2018 | |
| INVENTOR(S) | : Humbarger et al. | |

It is certified that error appears in the above-identified patent and that said Letters Patent is hereby corrected as shown below:

On the Title Page

Item [56], References Cited, under heading OTHER PUBLICATIONS, Replace the following:

"Borgias, "Synthetic, structural, and physical studies of titanium complexes of catechol and 3,5-di-tert-butylcatechol," Inorg. Chem., Apr. 1984, 23(8), 1009-1016." with --Borgias et al., "Synthetic, structural, and physical studies of titanium complexes of catechol and 3,5-di-tert-butylcatechol," Inorg. Chem., Apr. 1984, 23(8), 1009-1016.--

"Brezina, "Study of the reduction of oxygen on a carbon paste electrode in an alkaline medium," Coll. Czech. Chem. Commun., 1973, 38(10), 3024-3031." with --Březina et al., "Study of the reduction of oxygen on a carbon paste electrode in an alkaline medium," Coll. Czech. Chem. Commun., 1973, 38(10), 3024-3031.--

"Cerofontain et al. "Sulfonation and sulfation on reaction of 1,2- dihydroxybenzene and its methyl ethers in concentrated aqueous sulfuric acid," Recl Tray Chim Pays-Bas, 1988, pp. 325-330, vol. 107." with --Cerofontain et al. "Sulfonation and sulfation on reaction of 1,2- dihydroxybenzene and its methyl ethers in concentrated aqueous sulfuric acid," Recl des Trav Chim des Pays-Bas, 1988, pp. 325-330, vol. 107.--

"Chen, "Solution Redox Couples for Electrochemical Energy Storage: I. Iron (III)-Iron (II) Complexes with O-Phenanthroline and Related Ligands," Journal of the Electrochemical Society, Jul. 1981, 128(7), 1460-1467." with --Chen et al., "Solution Redox Couples for Electrochemical Energy Storage: I. Iron (III)-Iron (II) Complexes with O-Phenanthroline and Related Ligands," Journal of the Electrochemical Society, Jul. 1981, 128(7), 1460-1467.--

"Cohen, "The Association of Ferrocyanide Ions With Various Cations," J. Phys. Chem., Aug. 1957, 61(8), 1096-1100." with --Cohen et al., "The Association of Ferrocyanide Ions With Various Cations," J. Phys. Chem., Aug. 1957, 61(8), 1096-1100.--

Signed and Sealed this
Twenty-first Day of April, 2020

Andrei Iancu
*Director of the United States Patent and Trademark Office*

CERTIFICATE OF CORRECTION (continued)
U.S. Pat. No. 10,065,977 B2

"Davies, "Eiectroceramics from Source Materials via Molecular Intermediates: PbTi03 from Ti02 via [Ti(catecholate)3]2-" J. Am. Ceram. Soc., Aug. 1990, 73(8), 2570-2572." with --Davies et al., "Eiectroceramics from Source Materials via Molecular Intermediates: PbTi$O_3$ from Ti$O_2$ via [Ti(catecholate)$_3$]$^{2-}$" J. Am. Ceram. Soc., Aug. 1990, 73(8), 2570-2572.--

"Fryda, "Wastewater Treatment With Diamond Electrodes," Diamond Materials, Electrochemical Society Proceedings, 2000, 99(32), 473-483" with --Fryda et al., "Wastewater Treatment With Diamond Electrodes," Diamond Materials, Electrochemical Society Proceedings, 2000, 99(32), 473-483.--

"Gail, "Cyano Compounds, Inorganic" in Ullmann's Encyclopedia of Industrial Chemistry, 2012, 10, 674-710." with --Gail et al., "Cyano Compounds, Inorganic" in Ullmann's Encyclopedia of Industrial Chemistry, 2012, 10, 674-710.--

"Hollandsworth, "Zinc/Ferrocyanide Battery Development Phase IV" Lockheed Missiles and Space Company, Inc., Contractor report, Sandia Contract DE-AC04-76DP00789, May 1985, 278 pages." with --Hollandsworth et al., "Zinc/Ferricyanide Battery Development Phase IV" Lockheed Missiles and Space Company, Inc., Contractor report, Sandia Contract DE-AC04-76DP00789, May 1985, 278 pages.--

"Kim, "Novel catalytic effects of Mn304 for all vanadium redox flow batteries," Chem. Commun., Apr. 2012, 48(44), 5455-5457." with --Kim et al., "Novel catalytic effects of $Mn_3O_4$ for all vanadium redox flow batteries," Chem. Commun., Apr. 2012, 48(44), 5455-5457.--

"Kulesza, "Electrochemical preparation and characterization of hybrid films composed of Prussian blue type metal hexacyanoferrate and conducting polymer," Electrochimica Acta, Aug. 2001, 46(26-27), 4065-4073." with --Kulesza et al., "Electrochemical preparation and characterization of hybrid films composed of Prussian blue type metal hexacyanoferrate and conducting polymer," Electrochimica Acta, Aug. 2001, 46(26-27), 4065-4073.--

"Leung, "An undivided zinc-cerium redox flow battery operating at room temperature (295 K)," Electrochemistry Communications, 2011, vol. 13, pp. 770-773." with --Leung et al., "An undivided zinc-cerium redox flow battery operating at room temperature (295 K)," Electrochemistry Communications, 2011, vol. 13, pp. 770-773--

"Leung, "Ce(III)/Ce(iV) in methanesulfonic acid as the positive half cell of a redox flow battery," Electrochimica Acta, 2011, vol. 56, pp. 2145-2153" with --Leung et al., "Ce(III)/Ce(iV) in methanesulfonic acid as the positive half cell of a redox flow battery," Electrochimica Acta, 2011, vol. 56, pp. 2145-2153--

"Leung, "Zinc deposition and dissolution in methanesulfonic acid onto a carbon composite electrode as the negative electrode reactions in a hybrid redox flow battery," Electrochimica Acta, 2011, vol. 56, pp. 6536-6546." with --Leung et al., "Zinc deposition and dissolution in methanesulfonic acid onto a carbon composite electrode as the negative electrode reactions in a hybrid redox flow battery," Electrochimica Acta, 2011, vol. 56, pp. 6536-6546.--

"Leung, "Characterization of a zinc-cerium flow battery," Journal of Power Sources, 2011, vol. 195, pp. 5174-5185" with --Leung et al., "Characterization of a zinc-cerium flow battery," Journal of Power Sources, 2011, vol. 196, pp. 5174-5185.--

"Modiba, "Electrochemical impedance spectroscopy study of Ce(IV) with aminopolycarboxylate ligands for redox flow batteries applications," Journal of Power Sources, May 2012, vol. 205, 1-9." with --Modiba et al., "Electrochemical impedance spectroscopy study of Ce(IV) with aminopolycarboxylate ligands for redox flow batteries applications," Journal of Power Sources, May 2012, vol. 205, 1-9.--

"Modiba, "Electrochemical study of cerium(IV) in the presence of ethylenediaminetetraacetic acid (EDTA) and diethylenetriaminepentaacetate (DTPA) ligands," Journal of Applied Electrochemistry, Sep. 2008, 38(9), 1293-1299." with --Modiba et al., "Electrochemical study of cerium(IV) in the presence of ethylenediaminetetraacetic acid (EDTA) and diethylenetriaminepentaacetate (DTPA) ligands," Journal of Applied Electrochemistry, Sep. 2008, 38(9), 1293-1299--

"Nguyen, "Flow Batteries," The Electrochemical Society Interface, Fall2010, 19(3), 54-56." with --Nguyen et al., "Flow Batteries, "The Electrochemical Society Interface, Fall 2010, 19(3), 54-56.--

"Pharr, "Infrared Spectroelectrochemical Analysis of Adsorbed Hexacyanoferrate Species Formed during Potential Cycling in the Ferrocyanide/Ferricyanide Redox Couple," Anal. Chem., Nov. 1997, 69(22), 4673-4679." with --Pharr et al., "Infrared Spectroelectrochemical Analysis of Adsorbed Hexacyanoferrate Species Formed during Potential Cycling in the Ferrocyanide/Ferricyanide Redox Couple," Anal. Chem., Nov. 1997, 69(22), 4673-4679.--

"Raymond , "Coordination isomers of biological iron transport compounds. VI. Models of the enterobactin coordination site. A crystal field effect in the structure of potassium tris( catecholato ) chromate( III) and -ferrate( III) sesq u ihyd rates, K3[M( 02C6H4 )3].1. 5H20, M=chromium, iron," J. Am. Chem. Soc., Mar. 1976, 98(7), 1767-1774." with --Raymond et al., "Coordination Isomers of Biological Iron Transport Compounds. VI. Models of the enterobactin coordination site. A crystal field effect in the structure of potassium tris(catecholato) chromate(III) and - ferrate(III) sesquihydrates, $K_3[M(O_2C_6H_4)_3]$.cntdot.$1.5H_2O$, M = Cr, $Fe^1$, "J. Am. Chem. Soc., Mar. 1976, 98(7), 1767-1774.--

"Saito et al., "DPPH radical-scavenging reaction of protocatechuic acid: differnce in reactivity between acids and their esters," Helv Chim Acta, 2006, is 1395-1407, vol. 89." with --Saito et al., "DPPH (= 2,2-Diphenyl-1-picrylhydrazyl) Radical-Scavenging Reaction of Protocatechuic Acid (= 3,4-Dihydroxybenzoic Acid): Difference in Reactivity between Acids and Their Esters"--

"Sigma-Aldrich Tris(hydroxymethl)aminomethane, 2015." with --Sigma-Aldrich Tris(hydroxymethyl)aminomethane, 2015.--

"Sommer, "Titanium (IV) complexes with ligands having oxygen donor atoms in aqueous solutions," Zeitschrift fur Anorganische and Aligemeine Chemie, Mar. 1963, pp. 191-197, vol. 321, issue 3-4." with --Sommer, "Titanium (IV) complexes with ligands having oxygen donor atoms in aqueous

CERTIFICATE OF CORRECTION (continued)
U.S. Pat. No. 10,065,977 B2 solutions," Zeitschrift für anorganische und aligemeine Chemie , Mar. 1963, pp. 191-197, vol. 321, issue 3-4.--

"Steenken, "One-electron redox potentials of phenols. Hydroxy- and aminophenols and related compounds of biological interest," J. Phys. Chem., Sep. 1982, 86(18), 3661-3667." with --Steenken et al., "One-electron redox potentials of phenols. Hydroxy- and aminophenols and related compounds of biological interest," J. Phys. Chem., Sep. 1982, 86(18), 3661-3667.--

"Torres-Gomez, "Energy Storage in Hybrid Organic-Inorganic Materials Hexacyanoferrate-Doped Polypyrrole as Cathode in Reversible Lithium Cells," J. of the Electrochemical Society, 2000, 147(7), 2513-2516." with --Torres-Gomez et al., "Energy Storage in Hybrid Organic-Inorganic Materials Hexacyanoferrate-Doped Polypyrrole as Cathode in Reversible Lithium Cells," J. of the Electrochemical Society, 2000, 147(7), 2513-2516.--

"Wang, "Determination of iron, titanium, osmium, and aluminum with tiron by reversephase high Performance liquid chromatography/ electrochemistry," Microchem. J., Jun. 1991, 43(3), 191-197." with --Wang et al, "Determination of iron, titanium, osmium, and aluminum with tiron by reverse-phase high Performance liquid chromatography/ electrochemistry," Microchem. J., Jun. 1991, 43(3), 191-197.--

"Weber, "Redox flow batteries: a review," Journal of Applied Electrochemistry, Oct. 2011, 41(10), 1137-1164." with --Weber et al., "Redox flow batteries: a review," Journal of Applied Electrochemistry, Oct. 2011, 41(10), 1137-1164.--

"Westervelt, "A Study of the Calcium Complex of the Potassium Salt of Catechol-4-Sulfonate in Aqueous, Alkalino Media," Jan. 1981, Doctoral Dissertation, retrieved from https://smartech.gatech.edu/bitstrearn/handle/ 185 3/ 57 23/westervelt-iii hh. pdf." with --Westervelt, "A Study of the Calcium Complex of the Potassium Salt of Catechol-4-Sulfonate in Aqueous, Alkaline Media," Jan. 1981, Doctoral Dissertation, retrieved from https://smartech.gatech.edu/bitstrearn/handle/ 185 3/ 57 23/westervelt-iii hh. pdf.--

"Devi et al., "pH-metric investigation on Mixed-Ligand Complexs of Ca(II), Mg(II) and Zn(II) with L-Dopa and 1,10 Phenantroline in Propylene glycol-Water Mixtures," RRJC, Oct.-Dec. 2012, vol. 1, Issue 1, pp. 13-22." with --Devi et al., "pH-metric investigation on Mixed-Ligand Complexs of Ca(II), Mg(II) and Zn(II) with L-Dopa and 1,10 Phenanthroline in Propylene glycol-Water Mixtures," RRJC, Oct.-Dec. 2012, vol. 1, Issue 1, pp. 13-22.--

"Davies, "Eiectroceramics from Source Materials via Molecular Intermediates: $BaTlO_3$ from $TlO_2$ via [Ti( catecholate $)_3$ $]^{2-}$ ," May 1990, J. Am. Ceram. Soc., Aug. 1990, 73(5), 1429-30." with --Davies et al., "Electroceramics from Source Materials via Molecular Intermediates: $BaTiO_3$ from $TiO_2$ via [Ti( catecholate $)_3$ $]^{2-}$ ," May 1990, J. Am. Ceram. Soc., Aug. 1990, 73(5), 1429-30.--

In the Claims

In What is Claimed:

Under Column no. 23, (Line 39-40) Claim no. 1, Line no. 3-4, Replace:
"and (ii) a catalytic amount of an acid selected from the" with --(ii) acetic acid, and (iii) a catalytic amount of an acid selected from the--

Under Column no. 24, (Line 24) Claim no. 10, Line no. 2, Replace:
"complex has a formula of" with --complex has a formula of:--